(12) United States Patent
Boyd et al.

(10) Patent No.: US 8,093,248 B2
(45) Date of Patent: Jan. 10, 2012

(54) COMPOUNDS USEFUL FOR THE TREATMENT OF CONDITIONS ASSOCIATED WITH WEIGHT GAIN

(75) Inventors: Joseph W. Boyd, Cambridgeshire (GB); Giles A. Brown, Cambridge (GB); Michael Higginbottom, Cambridgeshire (GB); Viet-Anh Anne Horgan (Nee Nguyen), Redhill (GB); Jaqueline Ouzman, West Yorkshire (GB); Iain Simpson, Cambridge (GB)

(73) Assignee: AstraZeneca AB (PUBL), Sodertalje (SE)

( * ) Notice: Subject to any disclaimer, the term of this patent is extended or adjusted under 35 U.S.C. 154(b) by 250 days.

(21) Appl. No.: 12/315,831

(22) Filed: Dec. 5, 2008

(65) Prior Publication Data

US 2009/0281087 A1 Nov. 12, 2009

Related U.S. Application Data

(60) Provisional application No. 61/022,933, filed on Jan. 23, 2008.

(30) Foreign Application Priority Data

Dec. 5, 2007 (SE) ...................................... 0702697

(51) Int. Cl.
  C07D 295/185 (2006.01)
  C07D 401/12 (2006.01)
  A61K 31/496 (2006.01)
(52) U.S. Cl. .............. 514/252.11; 514/253.01; 544/357; 544/360
(58) Field of Classification Search .................. None
  See application file for complete search history.

(56) References Cited

U.S. PATENT DOCUMENTS

| | | | |
|---|---|---|---|
| 4,670,456 A | 6/1987 | Weber et al. | |
| 7,851,471 B2 * | 12/2010 | Boyd et al. .................. | 514/235.8 |
| 2009/0176798 A1 | 7/2009 | Boyd et al. | |
| 2009/0181967 A1 | 7/2009 | Boyd et al. | |
| 2009/0203695 A1 | 8/2009 | Higginbottom et al. | |

FOREIGN PATENT DOCUMENTS

| | | |
|---|---|---|
| EP | 0163260 | 5/1985 |
| EP | 0933361 | 8/1999 |
| EP | 1 787 679 | 5/2007 |
| JP | 2001-131149 | 5/2001 |
| JP | 2001-261657 | 9/2001 |
| SU | 1360583 | 5/1985 |
| WO | WO97/46585 | 12/1997 |
| WO | WO02/26723 | 4/2002 |
| WO | WO02/48124 | 6/2002 |
| WO | WO03/004480 | 1/2003 |
| WO | WO03084984 | 10/2003 |
| WO | WO2004055031 | 7/2004 |
| WO | WO2005016902 | 2/2005 |
| WO | WO2006060461 | 6/2006 |
| WO | WO2006072393 | 7/2006 |
| WO | WO2007003964 | 1/2007 |
| WO | WO2007/022257 | 2/2007 |
| WO | WO2007016496 | 2/2007 |
| WO | WO2007/025613 | 3/2007 |
| WO | WO2007/098939 | 9/2007 |
| WO | WO2008/025798 | 6/2008 |
| WO | WO2008/121592 | 10/2008 |
| WO | WO2008/147314 | 12/2008 |
| WO | WO2009/071668 | 6/2009 |
| WO | WO2009/147211 | 12/2009 |
| WO | WO2009/147216 | 12/2009 |
| WO | WO2009/147219 | 12/2009 |
| WO | WO2009/147221 | 12/2009 |

OTHER PUBLICATIONS

Banks, W.A. et al, "Leptin transport across the blood-brain barrier of the Koletsky rat is not mediated by a product of the leptin receptor gene", *Brain Res.* (2002), 950:130-136.
Bouloumie, A. et al, "Leptin, the Product of Ob Gene, Promotes Angiogenesis", *Circ. Res.* (1998), 83:1059-1066.
Browning et al, "Discrimination Ratio Analysis of Inflammatory Markers: Implications for the Study of Inflammation in Chronic Disease", *Metabolism* (2004), 53:899-903.
Bryson, J.M., "The future of leptin and leptin analogues in the treatment of obesity", *Diabetes, Obesity and Metabolism* (2000), 2:83-89.
Gonzalez et al, "Leptin$_{116-130}$ Stimulates Prolactin and Luteinizing Hormone Secretion in Fasted Adult Male Rats", *Neuroendocrinology* (1999), 70:213-220.
Gorden, P. et al, "The clinical uses of leptin", *Current Opinion in Pharmacology* (2003), 3:655-659.
Hanew, "The effects of human leptin fragment(126-140) on pituitary functions in man", *Eur. J. Endocrin.* (2003), 149:407-412.
Kastin, A.J., "Decreased transport of leptin across the blood-brain barrier in rats lacking the short form of the leptin receptor", *Peptides* (1999), 20:1449-1453.
Kinsella et al, "The aminoguanidine carboxylate BVT.12777 activates ATP-sensitive K$^+$channels in the rat insulinoma cell line, CR1-G1", *BMC Pharm* (2004), 4:17, 1-13.
Koistinen et al, "Circulating leptin has saturable transport into intrathecal space in humans", *Eur. J. Clin. Invest.* (1998), 28:894-897.

(Continued)

*Primary Examiner* — Emily Bernhardt
(74) *Attorney, Agent, or Firm* — Fish & Richardson P.C.

(57) ABSTRACT

The present application relates to new compounds of formula (I),

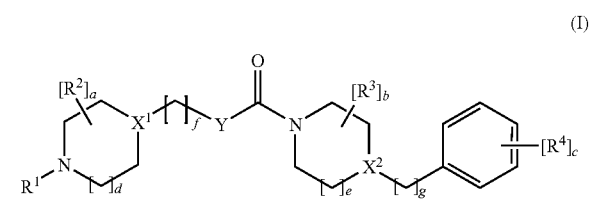

to pharmaceutical compositions comprising the compounds, to processes for their preparation, and to the use of the compounds as leptin receptor modulator mimetics in the preparation of medicaments against conditions associated with weight gain, type 2 diabetes and dyslipidemias.

17 Claims, 6 Drawing Sheets

OTHER PUBLICATIONS

Lu et al, "Leptin: A potential novel antidepressant", *Proc. Nat. Acad. Sci.*, (2006), 103:1593-1598.

Lyon, C.J. et al, "Minireview: Adiposity, Inflammation, and Atherogenesis", *Endocrinol.* (2003), 144:2195-2200.

Maachi et al, "Systemic low-grade inflammation is related to both circulating and adipose tissue TNFα, leptin and IL-6 levels in obese women", *Int. J. Obes. Relat. Metab. Disord.* (2004), 28:993-997.

Mangge et al, "Low Grade Inflammation in Juvenile Obesity and Type 1 Diabetes Associated with Early Signs of Atherosclerosis", *Exp. Clin. Endocrinol. Diabetes* (2004), 112:378-382.

Mantzoros, C.S., "The Role of Leptin in Human Obesity and Disease: A Review of Current Evidence", *Ann. Intern. Med. USA*,(1999), 130:671-680.

Mirshamsi et al, "BVT.3531 reduces body weight and activates $K_{ATP}$ channels in isolated arcuate neurons in rats", *Regulatory Peptides* (2007), 141:19-24.

Mirshamsi et al, "Activation of Hypothalamic ATP-Sensitive $K^+$ Channels by the Aminoguanidine Carboxylate BVT.12777", *J. Neuroendocrinology* (2005), 17, 246-254.

Otero, M. et al, "Leptin, from fat to inflammation: old questions and new insights", *FEBS Lett* (2005), 579:295-301.

Samson et al, "A 35 Amino Acid Fragment of Leptin Inhibits Feeding in the Rat", *Endocrinol.* (1996), 137:5182-5185.

Somasundar P. et al, "Leptin Is a Growth Factor in Cancer", *J. Surg. Res.* (2004), 116:337-349.

Suganami, E. et al, "Leptin Stimulates Ischemia-Induced Retinal Neovascularization—Possible Role of Vascular Endothelial Growth Factor Expressed in Retinal Endothelial Cells", *Diabetes* (2004), 53:2443-2448.

Van Heek et al, "Diet-induced Obese Mice Develop Peripheral, but Not Central, Resistance to Leptin", *J. Clin. Invest.* (1997), 99:385-390.

Zarkesh-Esfahani, H. et al, "High-Dose Leptin Activates Human Leukocytes Via Receptor Expression on Monocytes", *J. Immunol.* (2001), 167:4593-4599.

International Search Report for International Appln. No. PCT/EP2008/066877 dated Mar. 27, 2009 (2 pgs.).

International-Type Search Report for Sweden Patent Application SE0702696-6 dated Jun. 25, 2008 (8 pgs.).

STN International Registry File, RN: 913515-85-2 (Entry date Nov. 17, 2006) (1 pg.).

STN International Registry File, RN: 775282-94-5 (Entry date Nov. 5, 2004) (1 pg.).

International Search Report for International Patent Application PCT/EP2008/066899 (WO2009/071668) (PCT counterpart of the present application) dated Jun. 19, 2009.

International-Type Search Report for Sweden Patent Application 0702697-4 dated Jun. 25, 2008.

\* cited by examiner

COMPOUNDS USEFUL FOR THE TREATMENT OF CONDITIONS ASSOCIATED WITH WEIGHT GAIN

CROSS-REFERENCE TO RELATED APPLICATIONS

This application claims the benefit of Swedish Application No. 0702697-4, filed Dec. 5, 2007 and of U.S. Provisional Application No. 61/022,933, filed Jan. 23, 2008, the entire disclosures of which are hereby incorporated by reference in their entireties.

FIELD OF THE INVENTION

The present application relates to new piperazine derivatives, to pharmaceutical compositions comprising the compounds, to processes for their preparation, and to the use of the compounds as leptin receptor modulator mimetics in the preparation of medicaments against conditions associated with weight gain, type 2 diabetes and dyslipidemias.

BACKGROUND ART

The prevalence of obesity is increasing in the industrialized world. Typically, the first line of treatment is to offer diet and life style advice to patients, such as reducing the fat content of their diet and increasing their physical activity. However, some patients may also need to undergo drug therapy to maintain the beneficial results obtained from adapting the aforementioned diet and lifestyle changes.

Leptin is a hormone synthesized in fat cells that is believed to act in the hypothalamus to reduce food intake and body weight (see, e.g., Bryson, J. M. (2000) Diabetes, Obesity and Metabolism 2: 83-89).

It has been shown that in obese humans the ratio of leptin in the cerebrospinal fluid to that of circulating leptin is decreased (Koistinen et al., (1998) Eur. J. Clin. Invest. 28: 894-897). This suggests that the capacity for leptin transport into the brain is deficient in the obese state. Indeed, in animal models of obesity (NZO mouse and Koletsky rat), defects in leptin transport have been shown to result in reduced brain leptin content (Kastin, A. J. (1999) Peptides 20: 1449-1453; Banks, W. A. et al., (2002) Brain Res. 950: 130-136). In studies involving dietary-induced obese rodents (a rodent model that is believed to more closely resemble human obesity, see, e.g., Van Heek et al. (1997) J. Clin. Invest. 99: 385-390), excess leptin administered peripherally was shown to be ineffective in reducing food intake and body weight, whereas leptin injected directly into the brain was effective in reducing food intake and body weight. It has also been shown that in obese humans with excess circulating leptin, the signaling system became desensitized to the continual stimulation of the leptin receptors (Mantzoros, C. S. (1999) Ann. Intern. Med. 130: 671-680).

Amgen has conducted clinical trials with recombinant methionyl human leptin. The results from these trials were mixed, as even in the presence of high plasma concentrations of leptin weight loss was variable, and the average weight reduction in the cohort of patients tested relatively small (Obesity Strategic Perspective, Datamonitor, 2001).

Several attempts at finding active fragments have been reported in the literature since the discovery of the leptin gene coding sequence. An example is by Samson et al. (1996) Endocrinol. 137: 5182-5185 which describes an active fragment at the N-terminal (22 to 56). This sequence was shown to reduce food intake when injected ICV whereas a sequence taken at the C-terminal was shown not to have any effect. Leptin fragments are also disclosed in International Patent Application WO 97/46585.

Other reports looking at the C-terminus part of the sequence reported a possible stimulation of luteinising hormone production by a 116-130 fragment (Gonzalez et al., (1999) Neuroendocrinology 70:213-220) and an effect on GH production following GHRH administration (fragment 126-140) (Hanew (2003) Eur. J. Endocrin. 149: 407-412).

Leptin has recently been associated with inflammation. It has been reported that circulating leptin levels rise during bacterial infection and in inflammation (see Otero, M et al. (2005) FEBS Lett. 579: 295-301 and references therein). Leptin can also act to increase inflammation by enhancing the release of pro-inflammatory cytokines TNF and IL-6 from inflammatory cells (Zarkesh-Esfahani, H. et al. (2001) J. Immunol. 167: 4593-4599). These agents in turn can contribute to the insulin resistance commonly seen in obese patients by reducing the efficacy of insulin receptor signaling (Lyon, C. J. et al. (2003) Endocrinol. 44: 2195-2200). Continuous low grade inflammation is believed to be associated with obesity (in the presence and absence of insulin resistance and Type II diabetes) (Browning et al. (2004) Metabolism 53: 899-903, Inflammatory markers elevated in blood of obese women; Mangge et al. (2004) Exp. Clin. Endocrinol. Diabetes 112: 378-382, Juvenile obesity correlates with serum inflammatory marker C-reactive protein; Maachi et al. (2004) Int. J. Obes. Relat. Metab. Disord. 28: 993-997, Systemic low grade inflammation in obese people). Leptin has also been implicated in the process of atherogenesis, by promoting lipid uptake into macrophages and endothelial dysfunction, thus promoting the formation of atherosclerotic plaques (see Lyon, C. J. et al. (2003) Endocrinol. 144: 2195-2200).

Leptin has also been shown to promote the formation of new blood vessels (angiogenesis) a process implicated in the growth of adipose tissue (Bouloumie A, et al. (1998) Circ. Res. 83: 1059-1066). Angiogenesis has also been implicated in diabetic retinopathy (Suganami, E. et al. (2004) Diabetes. 53: 2443-2448).

Angiogenesis is also believed to be involved with the growth of new blood vessels that feed abnormal tumour cells. Elevated leptin levels have been associated with a number of cancers, in particular breast, prostate and gastrointestinal cancers in humans (Somasundar P. et al. (2004) J. Surg. Res. 116: 337-349).

Leptin receptor agonists may also be used in the manufacture of a medicament to promote wound healing (Gorden, P. and Gavrilova, O. (2003) Current Opinion in Pharmacology 3: 655-659).

Further, it has been shown that elevating leptin signaling in the brain may represent an approach for the treatment of depressive disorders (Lu, Xin-Yun et al. (2006) PNAS 103: 1593-1598).

DISCLOSURE OF THE INVENTION

It has surprisingly been found that compounds of formula (I) are effective in reducing body weight and food intake in rodents. While not wishing to be bound by theory, it is proposed that the compounds of formula I modulate the leptin receptor signaling pathway.

In some embodiments, compounds with leptin receptor agonistic like properties can be useful for the treatment of disorders relating to leptin signaling, as well as conditions associated with weight gain, such as obesity. The inventors hypothesized that small molecule CNS penetrant leptin mimetics would be able to by-pass the limiting uptake system into the brain. Further, assuming that this situation mirrors the human obese condition, the inventors believe that a CNS-active leptinoid with a relatively long duration of action would make an effective therapy for the obese state and its attendant complications, in particular (but not limited to) diabetes.

In other embodiments, compounds with leptin receptor antagonistic like properties could be useful for the treatment of inflammation, atherosclerosis, diabetic retinopathy and nephropathy.

In a first aspect, the disclosure relates to a compound of formula (I),

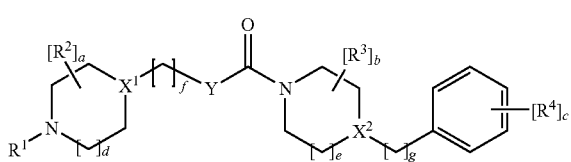

(I)

and pharmaceutically acceptable salts, hydrates, geometrical isomers, racemates, tautomers, optical isomers or N-oxides thereof, wherein:

$X^1$ and $X^2$ are each independently selected from N and CH;
$R^1$ is selected from hydrogen, $C_{1-6}$-alkyl (unsubstituted or optionally substituted with one or more substituents independently selected from halogen, hydroxy, cyano and $C_{1-6}$-alkoxy) and $C_{1-6}$-acyl (unsubstituted or optionally substituted with one or more substituents independently selected from halogen, hydroxy and $C_{1-6}$-alkoxy);
$R^2$ and $R^3$ are independently selected from hydrogen, halogen, hydroxy, $C_{1-6}$-alkyl (unsubstituted or optionally substituted with one or more substituents independently selected from halogen, hydroxy and $C_{1-6}$-alkoxy) and $C_{1-6}$-alkoxy (unsubstituted or optionally substituted with one or more substituents independently selected from halogen, hydroxy and $C_{1-6}$-alkoxy);
$R^4$ is independently selected from hydrogen, halogen, hydroxy, cyano, nitro, $CF_3$, $C_{1-6}$-alkyl and $C_{1-6}$-alkoxy;
Y is O, $C(R^{5A})(R^{5B})$ or $N(R^6)$;
$R^{5A}$ and $R^{5B}$ are each independently $C_{1-4}$-alkyl, or form, together with the carbon atom to which they are attached, a 3- to 6-membered cycloalkyl ring;
$R^6$ is hydrogen or $C_{1-4}$-alkyl;
a, b and c are each independently 1, 2 or 3;
d and e are each independently 0, 1 or 2;
f is 0, 1, 2 or 3; and
g is 0, 1 or 2;
with the proviso that the compound is not selected from the group consisting of:
4-(2,4-dimethylphenyl)-N-(1-methyl-4-piperidinyl)-1-piperazinecarboxamide;
N-(1-methyl-4-piperidinyl)-4-(phenylmethyl)-1-piperidinecarboxamide;
4-benzyl-N-[2-(4-methyl-1-piperazinyl)ethyl]-1-piperidinecarboxamide;
4-(3-methylphenyl)-N-(1-methyl-4-piperidinyl)-1-piperazinecarboxamide;
4-(4-chlorophenyl)-N-(1-methyl-4-piperidinyl)-1-piperazinecarboxamide;
N-[2-(4-methyl-1-piperazinyl)ethyl]-4-phenyl-1-piperazinecarboxamide;
4-(3,4-dimethylphenyl)-N-(1-methyl-4-piperidinyl)-1-piperazinecarboxamide;
4-(2-methoxyphenyl)-N-(1-methyl-4-piperidinyl)-1-piperazinecarboxamide;
4-(2-chlorophenyl)-N-(1-methyl-4-piperidinyl)-1-piperazinecarboxamide;
N-[3-(4-methyl-1-piperazinyl)propyl]-4-phenyl-1-piperazinecarboxamide;
4-(2-hydroxyphenyl)-N-(1-methyl-4-piperidinyl)-1-piperazinecarboxamide;
N-(1-methyl-4-piperidinyl)-4-(4-nitrophenyl)-1-piperazinecarboxamide;
2-(4-piperidinyl)ethyl 4-phenylpiperazine-1-carboxylate; and
3-methyl-4-(3-methylphenyl)-N-(1-methyl-4-piperidinyl)-1-piperazinecarboxamide.

Y is preferably O or $C(R^{5A})(R^{5B})$
$X^2$ is preferably N.
$R^1$ is preferably selected from hydrogen, $C_{1-4}$-alkyl and $C_{1-4}$-alkoxy-$C_{1-4}$-alkyl.

In a most preferred embodiment, $R^1$ is hydrogen, methyl, ethyl or methoxyethyl.

$R^2$ and $R^3$ are preferably independently selected from hydrogen and $C_{1-4}$-alkyl.

In a most preferred embodiment, $R^2$ and $R^3$ are hydrogen.

$R^4$ is preferably independently selected from hydrogen, halogen, $CF_3$, $C_{1-4}$-alkyl and $C_{1-4}$-alkoxy.

In a most preferred embodiment, $R^4$ is independently selected from hydrogen, fluoro, chloro, $CF_3$, methyl and methoxy.

$R^{5A}$ and $R^{5B}$ are preferably both methyl, or form, together with the carbon atom to which they are attached, a cyclopentyl ring.

d and e are preferably 1.
f is preferably 1 or 2.
g is preferably 0 or 1.
Particular preferred compounds of formula (I) are the compounds of formula (I')

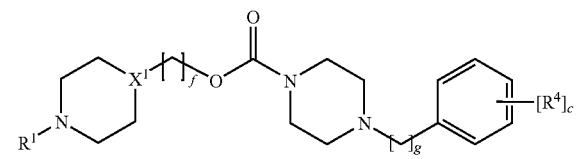

(I')

wherein $X^1$, $R^1$, $R^4$, c, f and g are as defined in formula (I).

Specific preferred compounds of formula (I) are those selected from the group consisting of:
(1-methylpiperidin-4-yl)methyl 4-phenylpiperazine-1-carboxylate;
(1-methylpiperidin-4-yl)methyl 4-(4-chlorophenyl)piperazine-1-carboxylate;
piperidin-4-ylmethyl 4-(4-methylphenyl)piperazine-1-carboxylate;
(1-methylpiperidin-4-yl)methyl 4-(4-methylphenyl)piperazine-1-carboxylate;
(1-methylpiperidin-4-yl)methyl 4-(3-methylphenyl)piperazine-1-carboxylate;
(1-methylpiperidin-4-yl)methyl 4-(4-fluorophenyl)piperazine-1-carboxylate;
(1-methylpiperidin-4-yl)methyl 4-(4-methoxyphenyl)piperazine-1-carboxylate;
[1-(2-methoxyethyl)piperidin-4-yl]methyl 4-phenylpiperazine-1-carboxylate;

[1-(2-methoxyethyl)piperidin-4-yl]methyl 4-(4-fluorophenyl)piperazine-1-carboxylate;
[1-(2-methoxyethyl)piperidin-4-yl]methyl 4-(4-chlorophenyl)piperazine-1-carboxylate;
[1-(2-methoxyethyl)piperidin-4-yl]methyl 4-(4-methylphenyl)piperazine-1-carboxylate;
[1-(2-methoxyethyl)piperidin-4-yl]methyl 4-(4-methoxyphenyl)piperazine-1-carboxylate;
2-(1-methylpiperidin-4-yl)ethyl 4-(4-methylphenyl)piperazine-1-carboxylate;
1-methylpiperidin-4-yl 4-(4-methylphenyl)piperazine-1-carboxylate;
[(3S)-1-methylpyrrolidin-3-yl]-4-(4-methylphenyl)piperazine-1-carboxylate;
2-(4-methylpiperazin-1-yl)ethyl 4-phenylpiperazine-1-carboxylate;
2-(4-methylpiperazin-1-yl)ethyl 4-(4-chlorophenyl)piperazine-1-carboxylate;
2-(4-methylpiperazin-1-yl)ethyl 4-(3-trifluoromethylphenyl)piperazine-1-carboxylate;
2-(4-methylpiperazin-1-yl)ethyl 4-(3-fluorophenyl)piperazine-1-carboxylate;
2-(4-methylpiperazin-1-yl)ethyl 4-(2-methylphenyl)piperazine-1-carboxylate;
2-(4-methylpiperazin-1-yl)ethyl 4-(4-methylphenyl)piperazine-1-carboxylate;
2-(4-methylpiperazin-1-yl)ethyl 4-(2,5-dimethylphenyl)piperazine-1-carboxylate;
2-(4-methylpiperazin-1-yl)ethyl 4-(3,4-dichlorophenyl)piperazine-1-carboxylate;
2-(4-methylpiperazin-1-yl)ethyl 4-(2,4-difluorophenyl)piperazine-1-carboxylate;
2-(4-methylpiperazin-1-yl)ethyl 4-(4-methoxyphenyl)piperazine-1-carboxylate;
2-(4-methylpiperazin-1-yl)ethyl 3-methyl-4-(3-methylphenyl)piperazine-1-carboxylate;
2-(4-methylpiperazin-1-yl)ethyl 4-benzylpiperazine-1-carboxylate;
2-(4-methylpiperazin-1-yl)ethyl 4-phenylpiperidine-1-carboxylate;
2-(4-methylpiperazin-1-yl)ethyl 3-phenylpyrrolidine-1-carboxylate;
2-piperazin-1-ylethyl 4-phenylpiperazine-1-carboxylate;
2-(4-(2-methoxyethyl)piperazin-1-yl)ethyl 4-phenylpiperazine-1-carboxylate;
2-(4-ethylpiperazin-1-yl)ethyl 4-phenylpiperazine-1-carboxylate;
2-(4-methyl-1,4-diazepan-1-yl)ethyl 4-(4-methylphenyl)piperazine-1-carboxylate;
3-(4-methylpiperazin-1-yl)propyl 4-phenylpiperazine-1-carboxylate;
1-[2,2-dimethyl-3-(4-methylpiperazin-1-yl)propanoyl]-4-phenylpiperazine;
1-{2,2-dimethyl-3-[4-(4-chlorophenyl)piperazin-1-yl]-3-oxopropyl}-4-methylpiperazine;
1-{2,2-dimethyl-3-[4-(4-methylphenyl)piperazin-1-yl]-3-oxopropyl}-4-methylpiperazine;
1-{2,2-dimethyl-3-[4-(4-methylphenyl)piperazin-1-yl]-3-oxopropyl}-4-ethylpiperazine;
1-[2,2-dimethyl-3-(4-methylpiperazin-1-yl)propanoyl]-4-(4-fluorophenyl)piperazine;
1-methyl-4-[(1-{[4-(4-methylphenyl)piperazin-1-yl]carbonyl}cyclopentyl)methyl]piperazine;
2-(4-methylpiperazin-1-yl)ethyl 4-(4-fluorophenyl)piperazine-1-carboxylate;
2-(4-methylpiperazin-1-yl)ethyl 4-(4-fluorobenzyl)piperazine-1-carboxylate;
2-(4-methylpiperazin-1-yl)ethyl 4-(4-chlorobenzyl)piperazine-1-carboxylate; and
2-(4-Methylpiperazin-1-yl)ethyl 4-[2-(4-chlorophenyl)ethyl]piperazine-1-carboxylate.

Another aspect of the present disclosure is a compound of formula (I) for use in therapy.

In a further aspect, the disclosure relates to a compound of formula (I) for use in the treatment or prevention of any of the disorders or conditions described herein.

In yet a further aspect, the invention relates to the use of a compound of formula (I) in the manufacture of a medicament for the treatment or prevention of any of the disorders or conditions described herein.

In some embodiments, said compounds may be used in the manufacture of a medicament for the treatment or prevention of a condition that is prevented, treated, or ameliorated by selective action on the leptin receptor.

In some embodiments, said compounds may be used in the manufacture of a medicament for the treatment or prevention of conditions (in particular, metabolic conditions) that are associated with weight gain. Conditions associated with weight gain include diseases, disorders, or other conditions that have an increased incidence in obese or overweight subjects. Examples include: lipodystrophy, HIV lipodystrophy, diabetes (type 2), insulin resistance, metabolic syndrome, hyperglycemia, hyperinsulinemia, dyslipidemia, hepatic steatosis, hyperphagia, hypertension, hypertriglyceridemia, infertility, a skin disorder associated with weight gain, macular degeneration. In some embodiments, the compounds may also be used in the manufacture of a medicament for maintaining weight loss of a subject.

In some embodiments, compounds of formula (I) which are leptin receptor agonist mimetics may also be used in the manufacture of a medicament to promote wound healing.

In some embodiments, compounds of formula (I) which are leptin receptor agonist mimetics may also be used in the manufacture of a medicament for the treatment or prevention of conditions that cause a decrease in circulating leptin concentrations, and the consequent malfunction of the immune and reproductive systems. Examples of such conditions and malfunctions include severe weight loss, dysmenorrhea, amenorrhea, female infertility, immunodeficiency and conditions associated with low testosterone levels.

In some embodiments, compounds of formula (I) which are leptin receptor agonist mimetics may also be used in the manufacture of a medicament for the treatment or prevention of conditions caused as a result of leptin deficiency, or a leptin or leptin receptor mutation.

In some other embodiments, compounds of formula (I) which are leptin receptor antagonist mimetics may be used for the treatment or prevention of inflammatory conditions or diseases, low level inflammation associated with obesity and excess plasma leptin and in reducing other complications associated with obesity including atherosclerosis, and for the correction of insulin resistance seen in Metabolic Syndrome and diabetes.

In some embodiments, compounds of formula (I) which are leptin receptor antagonist mimetics can be used for the treatment or prevention of inflammation caused by or associated with: cancer (such as leukemias, lymphomas, carcinomas colon cancer, breast cancer, lung cancer, pancreatic cancer, hepatocellular carcinoma, kidney cancer, melanoma, hepatic, lung, breast, and prostate metastases, etc.); autoimmune disease (such as organ transplant rejection, lupus erythematosus, graft v. host rejection, allograft rejections, multiple sclerosis, rheumatoid arthritis, type I diabetes mellitus including the destruction of pancreatic islets leading to diabetes and the inflammatory consequences of diabetes); autoimmune damage (including multiple sclerosis, Guillam Barre Syndrome, myasthenia gravis); cardiovascular conditions associated with poor tissue perfusion and inflammation (such as atheromas, atherosclerosis, stroke, ischaemia-reperfusion injury, claudication, spinal cord injury, congestive heart failure, vasculitis, haemorrhagic shock, vasospasm following subarachnoid haemorrhage, vasospasm following cerebrovascular accident, pleuritis, pericarditis, the cardiovascular complications of diabetes); ischaemia-reperfusion injury, ischaemia and associated inflammation, restenosis following angioplasty and inflammatory aneurysms; epilepsy, neurodegeneration (including Alzheimer's Disease), arthritis (such as rheumatoid arthritis, osteoarthritis, rheumatoid spondylitis, gouty arthritis), fibrosis (for example of the lung, skin and liver), multiple sclerosis, sepsis, septic shock, encephalitis, infectious arthritis, Jarisch-Herxheimer reaction, shingles, toxic shock, cerebral malaria, Lyme's disease, endotoxic shock, gram negative shock, haemorrhagic shock, hepatitis (arising both from tissue damage or viral infection), deep vein thrombosis, gout; conditions associated with breathing difficulties (e.g. chronic obstructive pulmonary disease, impeded and obstructed airways, bronchoconstriction, pulmonary vasoconstriction, impeded respiration, chronic pulmonary inflammatory disease, silicosis, pulmonary sarcosis, cystic fibrosis, pulmonary hypertension, pulmonary vasoconstriction, emphysema, bronchial allergy and/or inflammation, asthma, hay fever, rhinitis, vernal conjunctivitis and adult respiratory distress syndrome); conditions associated with inflammation of the skin (including psoriasis, eczema, ulcers, contact dermatitis); conditions associated with inflammation of the bowel (including Crohn's disease, ulcerative colitis and pyresis, irritable bowel syndrome, inflammatory bowel disease); HIV (particularly HIV infection), cerebral malaria, bacterial meningitis, osteoporosis and other bone resorption diseases, osteoarthritis, infertility from endometriosis, fever and myalgia due to infection, and other conditions mediated by excessive anti-inflammatory cell (including neutrophil, eosinophil, macrophage and T-cell) activity.

In some embodiments, compounds of formula (I) which are leptin receptor antagonists mimetics may be used for the treatment or prevention of macro or micro vascular complications of type 1 or 2 diabetes, retinopathy, nephropathy, autonomic neuropathy, or blood vessel damage caused by ischaemia or atherosclerosis.

In some embodiments, compounds of formula (I) which are leptin receptor antagonist mimetics may be used to inhibit angiogenesis. Compounds that inhibit angiogenesis may be used for the treatment or prevention of obesity or complications associated with obesity. Compounds that inhibit angiogenesis may be used for the treatment or prevention of complications associated with inflammation diabetic retinopathy, or tumour growth particularly in breast, prostate or gastrointestinal cancer.

In a further aspect, the disclosure relates to a method for the treatment or prevention of any of the disorders or conditions described herein, which includes administering to a subject (e.g., a subject in need thereof, e.g., a mammal) an effective amount of a compound of formula I.

Methods delineated herein include those wherein the subject is identified as in need of a particular stated treatment. Identifying a subject in need of such treatment can be in the judgment of a subject or a health care professional and can be subjective (e.g. opinion) or objective (e.g. measurable by a test or diagnostic method).

In other aspects, the methods herein include those further comprising monitoring subject response to the treatment administrations. Such monitoring may include periodic sampling of subject tissue, fluids, specimens, cells, proteins, chemical markers, genetic materials, etc. as markers or indicators of the treatment regimen. In other methods, the subject is prescreened or identified as in need of such treatment by assessment for a relevant marker or indicator of suitability for such treatment.

In one embodiment, the disclosure provides a method of monitoring treatment progress. The method includes the step of determining a level of diagnostic marker (Marker) (e.g., any target or cell type delineated herein modulated by a compound herein) or diagnostic measurement (e.g., screen, assay) in a subject suffering from or susceptible to a disorder or symptoms thereof delineated herein, in which the subject has been administered a therapeutic amount of a compound herein sufficient to treat the disease or symptoms thereof. The level of Marker determined in the method can be compared to known levels of Marker in either healthy normal controls or in other afflicted patients to establish the subject's disease status. In preferred embodiments, a second level of Marker in the subject is determined at a time point later than the determination of the first level, and the two levels are compared to monitor the course of disease or the efficacy of the therapy. In certain preferred embodiments, a pre-treatment level of Marker in the subject is determined prior to beginning treatment according to this disclosure; this pre-treatment level of Marker can then be compared to the level of Marker in the subject after the treatment commences, to determine the efficacy of the treatment.

In certain method embodiments, a level of Marker or Marker activity in a subject is determined at least once. Comparison of Marker levels, e.g., to another measurement of Marker level obtained previously or subsequently from the same patient, another patient, or a normal subject, may be useful in determining whether therapy according to the disclosure is having the desired effect, and thereby permitting adjustment of dosage levels as appropriate. Determination of Marker levels may be performed using any suitable sampling/expression assay method known in the art or described herein. Preferably, a tissue or fluid sample is first removed from a subject. Examples of suitable samples include blood, urine, tissue, mouth or cheek cells, and hair samples containing roots. Other suitable samples would be known to the person skilled in the art. Determination of protein levels and/or mRNA levels (e.g., Marker levels) in the sample can be performed using any suitable technique known in the art, including, but not limited to, enzyme immunoassay, ELISA, radiolabeling/assay techniques, blotting/chemiluminescence methods, real-time PCR, and the like.

In some embodiments, it may be advantageous if a compound of formula (I) is able to penetrate the central nervous system. In other embodiments, it may be advantageous if a compound of formula (I) is not able to penetrate the CNS. In general, it is expected that compounds that are leptin receptor agonist mimetics may be particularly useful for the treatment or prevention of obesity, insulin resistance, or diabetes (particularly glucose intolerance) if these compounds can penetrate the CNS. A person of ordinary skill in the art can readily determine whether a compound can penetrate the CNS. A suitable method that may be used is described in the Biological Methods section.

A leptin receptor response may be measured in any suitable way. In vitro, this may be done be measuring leptin receptor signaling. For example, phosphorylation of Akt, STAT3, STAT5, MAPK, shp2 or the leptin receptor in response to binding of leptin or a compound of the disclosure to the leptin receptor may be measured. The extent of phosphorylation of Akt, STAT3, STAT5, MAPK, shp2 or the leptin receptor may be determined for example by Western blotting or by ELISA. Alternatively, a STAT reporter assay may be used, for example STAT driven luciferase expression. A cell line expressing the leptin receptor may be used for such assays. In vivo, leptin receptor response may be measured by determining the reduction in food intake and body weight after administration of leptin or a compound of the disclosure.

The Biological Methods below describe assays and methods that can be used to determine whether a compound of the disclosure is a leptin receptor agonist mimetic or a leptin receptor antagonist mimetic.

A compound of formula (I) may be administered with or without other therapeutic agents. For example, where it is desired to reduce inflammation, the compound may be administered with an anti-inflammatory agent (for example, disease modifying anti-rheumatic drugs such as methotrexate, sulphasalazine and cytokine inactivating agents, steroids, NSAIDs, cannabinoids, tachykinin modulators, or bradykinin modulators). Where it is desired to provide an anti-tumour effect, a compound of formula (I) may be administered with a cytotoxic agent (for example, methotrexate, cyclophosphamide) or another anti-tumour drug.

Compounds of formula (I) may be radiolabeled (for example with tritium or radioactive iodine) for in vitro or in vivo applications, such as receptor displacement studies or receptor imaging.

A further aspect of the present disclosure relates to processes for the manufacture of compounds of formula (I) as defined above. In one embodiment, the process comprises:

(a) reacting a compound of formula (II):

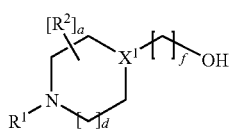

(II)

wherein $X^1$, $R^1$, $R^2$, a, d and f are as defined in formula (I), with 4-nitrophenyl chloroformate or bis-(4-nitrophenyl)carbonate in the presence of a suitable base (such as DIPEA or NMM) in a suitable solvent (such as DCM), at −10 to 40° C., to form a compound of formula (III):

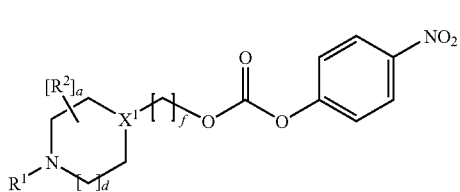

(III)

(b) reacting the compound of formula (III) with a compound of formula (IV):

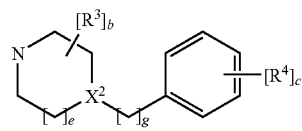

(IV)

wherein $X^2$, $R^3$, $R^4$, b, c, e and g are as defined in formula (I), in the presence of a suitable base, (such as DIPEA), in a suitable solvent (such as DMF), at −10 to 40° C., to obtain a compound of formula (I); and (c) optionally, in one or several steps transforming a compound of formula (I) into another compound of formula (I).

In another embodiment, the process comprises:

(a) reacting a compound of formula (IV):

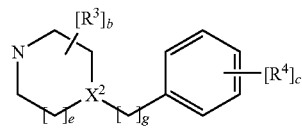

(IV)

wherein $X^2$, $R^3$, $R^4$, b, c, e and g are as defined in formula (I), with a compound of formula (V):

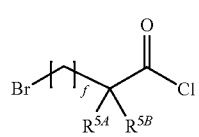

(V)

wherein $R^{5A}$, $R^{5B}$ and f are as defined in formula (I), in the presence of a suitable base (such as DIPEA), in a suitable solvent (such as DCM), at −10 to 40° C., to obtain a compound of formula (VI):

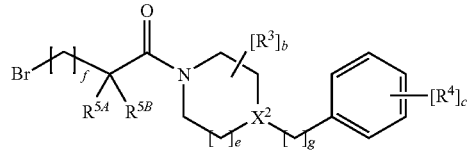

(VI)

(b) reacting the compound of formula (VI) with a compound of formula (VII):

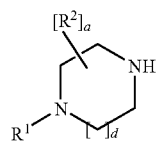

(VII)

wherein $R^1$, $R^2$, a and d are as defined in formula (I),
in a suitable solvent (such as N-methylpyrrolidinone), at elevated temperature, to obtain a compound of formula (I); and (c) optionally, in one or several steps transforming a compound of formula (I) into another compound of formula (I).

DEFINITIONS

The following definitions shall apply throughout the specification and the appended claims.

Unless otherwise stated or indicated, the term "$C_{1-6}$-alkyl" denotes a straight or branched alkyl group having from 1 to 6 carbon atoms. Examples of said $C_{1-6}$-alkyl include methyl, ethyl, n-propyl, iso-propyl, n-butyl, iso-butyl, sec-butyl, t-butyl, and straight- and branched-chain pentyl and hexyl. For parts of the range "$C_{1-6}$-alkyl" all subgroups thereof are contemplated such as $C_{1-5}$-alkyl, $C_{1-4}$-alkyl, $C_{1-3}$-alkyl, $C_{1-2}$-alkyl, $C_{2-6}$-alkyl, $C_{2-5}$-alkyl, $C_{2-4}$-alkyl, $C_{2-3}$-alkyl, $C_{3-6}$-alkyl, $C_{4-5}$-alkyl, etc.

Unless otherwise stated or indicated, the term "$C_{1-6}$-acyl" denotes a carbonyl group that is attached through its carbon atom to a hydrogen atom (i.e., a formyl group) or to a straight or branched $C_{1-5}$-alkyl group, where alkyl is defined as above. Examples of said $C_{1-6}$-acyl include formyl, acetyl, propionyl, n-butyryl, 2-methylpropionyl and n-pentoyl. For parts of the range "$C_{1-6}$-acyl" all subgroups thereof are contemplated such as $C_{1-5}$-acyl, $C_{1-4}$-acyl, $C_{1-3}$-acyl, $C_{1-2}$-acyl, $C_{2-6}$-acyl, $C_{2-5}$-acyl, $C_{2-4}$-acyl, $C_{2-3}$-acyl, $C_{3-6}$-acyl, $C_{4-5}$-acyl, etc. If a $C_{1-6}$-acyl group is optionally substituted with one or more substituents independently selected from halogen, hydroxy and $C_{1-6}$-alkoxy, said substituent can not be attached to the carbonyl carbon atom.

Unless otherwise stated or indicated, the term "$C_{1-6}$-alkoxy" denotes a straight or branched alkoxy group having from 1 to 6 carbon atoms. Examples of said $C_{1-6}$-alkoxy include methoxy, ethoxy, n-propoxy, iso-propoxy, n-butoxy, iso-butoxy, sec-butoxy, t-butoxy, and straight- and branched-chain pentoxy and hexoxy. For parts of the range "$C_{1-6}$-alkoxy" all subgroups thereof are contemplated such as $C_{1-5}$-alkoxy, $C_{1-4}$-alkoxy, $C_{1-3}$-alkoxy, $C_{1-2}$-alkoxy, $C_{2-6}$-alkoxy, $C_{2-15}$-alkoxy, $C_{2-4}$-alkoxy, $C_{2-3}$-alkoxy, $C_{3-6}$-alkoxy, $C_{4-5}$-alkoxy, etc.

"Halogen" refers to fluorine, chlorine, bromine or iodine.

"Hydroxy" refers to the —OH radical.

"Nitro" refers to the —$NO_2$ radical.

"Cyano" refers to the —CN radical.

"Optional" or "optionally" means that the subsequently described event or circumstance may but need not occur, and that the description includes instances where the event or circumstance occurs and instances in which it does not.

The term "mammal" includes organisms, which include mice, rats, cows, sheep, pigs, rabbits, goats, and horses, monkeys, dogs, cats, and preferably humans. The subject may be a human subject or a non human animal, particularly a domesticated animal, such as a dog. "Pharmaceutically acceptable" means being useful in preparing a pharmaceutical composition that is generally safe, non-toxic and neither biologically nor otherwise undesirable and includes being useful for veterinary use as well as human pharmaceutical use.

"Treatment" as used herein includes prophylaxis of the named disorder or condition, or amelioration or elimination of the disorder once it has been established.

"An effective amount" refers to an amount of a compound that confers a therapeutic effect (e.g., treats, controls, ameliorates, prevents, delays the onset of, or reduces the risk of developing a disease, disorder, or condition or symptoms thereof) on the treated subject.

The therapeutic effect may be objective (i.e., measurable by some test or marker) or subjective (i.e., subject gives an indication of or feels an effect).

"Prodrugs" refers to compounds that may be converted under physiological conditions or by solvolysis to a biologically active compound of formula (I). A prodrug may be inactive when administered to a subject in need thereof, but is converted in vivo to an active compound of formula (I). Prodrugs are typically rapidly transformed in vivo to yield the parent compound, e.g. by hydrolysis in the blood. The prodrug compound usually offers advantages of solubility, tissue compatibility or delayed release in a mammalian organism (see Silverman, R. B., *The Organic Chemistry of Drug Design and Drug Action*, $2^{nd}$ Ed., Elsevier Academic Press (2004), pp. 498-549). Prodrugs may be prepared by modifying functional groups, such as a hydroxy, amino or mercapto groups, present in a compound of formula (I) in such a way that the modifications are cleaved, either in routine manipulation or in vivo, to the parent compound. Examples of prodrugs include, but are not limited to, acetate, formate and succinate derivatives of hydroxy functional groups or phenyl carbamate derivatives of amino functional groups.

Throughout the specification and the appended claims, a given chemical formula or name shall also encompass all hydrates and solvates thereof. Further, a given chemical formula or name shall encompass all tautomeric and stereoisomeric forms thereof. Stereoisomers include enantiomers and diastereomers. Enantiomers can be present in their pure forms, or as racemic (equal) or unequal mixtures of two enantiomers. Diastereomers can be present in their pure forms, or as mixtures of diastereomers. Diastereomers also include geometrical isomers, which can be present in their pure cis or trans forms or as mixtures of those.

The compounds of formula (I) may be used as such or, where appropriate, as pharmacologically acceptable salts (acid or base addition salts) thereof. The pharmacologically acceptable addition salts mentioned below are meant to comprise the therapeutically active non-toxic acid and base addition salt forms that the compounds are able to form. Compounds that have basic properties can be converted to their pharmaceutically acceptable acid addition salts by treating the base form with an appropriate acid. Exemplary acids include inorganic acids, such as hydrogen chloride, hydrogen bromide, hydrogen iodide, sulphuric acid, phosphoric acid; and organic acids such as formic acid, acetic acid, propanoic acid, hydroxyacetic acid, lactic acid, pyruvic acid, glycolic acid, maleic acid, malonic acid, oxalic acid, benzenesulphonic acid, toluenesulphonic acid, methanesulphonic acid, trifluoroacetic acid, fumaric acid, succinic acid, malic acid, tartaric acid, citric acid, salicylic acid, p-aminosalicylic acid, pamoic acid, benzoic acid, ascorbic acid and the like. Exemplary base addition salt forms are the sodium, potassium, calcium salts, and salts with pharmaceutically acceptable amines such as, for example, ammonia, alkylamines, benzathine, and amino acids, such as, e.g. arginine and lysine. The term addition salt as used herein also comprises solvates which the compounds and salts thereof are able to form, such as, for example, hydrates, alcoholates and the like.

Compositions

For clinical use, the compounds of the disclosure are formulated into pharmaceutical formulations for various modes of administration. It will be appreciated that the compounds may be administered together with a physiologically acceptable carrier, excipient, or diluent. The pharmaceutical compositions may be administered by any suitable route, preferably by oral, rectal, nasal, topical (including buccal and sublingual), sublingual, transdermal, intrathecal, transmucosal or parenteral (including subcutaneous, intramuscular, intravenous and intradermal) administration.

Other formulations may conveniently be presented in unit dosage form, e.g., tablets and sustained release capsules, and in liposomes, and may be prepared by any methods well known in the art of pharmacy. Pharmaceutical formulations are usually prepared by mixing the active substance, or a pharmaceutically acceptable salt thereof, with conventional pharmaceutically acceptable carriers, diluents or excipients. Examples of excipients are water, gelatin, gum arabicum, lactose, microcrystalline cellulose, starch, sodium starch glycolate, calcium hydrogen phosphate, magnesium stearate, talcum, colloidal silicon dioxide, and the like. Such formulations may also contain other pharmacologically active agents, and conventional additives, such as stabilizers, wetting agents, emulsifiers, flavouring agents, buffers, and the like. Usually, the amount of active compounds is between 0.1-95% by weight of the preparation, preferably between 0.2-20% by weight in preparations for parenteral use and more preferably between 1-50% by weight in preparations for oral administration.

The formulations can be further prepared by known methods such as granulation, compression, microencapsulation, spray coating, etc. The formulations may be prepared by conventional methods in the dosage form of tablets, capsules, granules, powders, syrups, suspensions, suppositories or injections. Liquid formulations may be prepared by dissolving or suspending the active substance in water or other suitable vehicles. Tablets and granules may be coated in a conventional manner. To maintain therapeutically effective plasma concentrations for extended periods of time, compounds of the disclosure may be incorporated into slow release formulations.

The dose level and frequency of dosage of the specific compound will vary depending on a variety of factors including the potency of the specific compound employed, the metabolic is stability and length of action of that compound, the patient's age, body weight, general health, sex, diet, mode and time of administration, rate of excretion, drug combination, the severity of the condition to be treated, and the patient undergoing therapy. The daily dosage may, for example, range from about 0.001 mg to about 100 mg per kilo of body weight, administered singly or multiply in doses, e.g. from about 0.01 mg to about 25 mg each. Normally, such a dosage is given orally but parenteral administration may also be chosen.

Preparation of Compounds of the Invention

The compounds of formula (I) above may be prepared by, or in analogy with, conventional methods. Formation of the central urethane linker is the key synthetic step in preparing the carbamate compounds formula (I). A large number of activating reagents can be used for the formation of a urethane linker e.g. phosgene to form chloroformate of alcohols, or carbonyldiimidazole (CDI) to form imidazole carboxylates. Typically the urethane linkers incorporated into compounds of formula (I) have been synthesized utilizing 4-nitrophenyl chloroformate or bis-(4-nitrophenyl)carbonate as the activating agent. The preparation of intermediates and compounds according to the examples of the present disclosure may in particular be illuminated by the following Schemes 1 and 2. Definitions of variables in the structures in the schemes herein are commensurate with those of corresponding positions in the formulae delineated herein.

Typically, the synthesis of carbamate compounds of formula (I) is performed by activation of the alcohol moiety.

Treatment of alcohol (II) with 4-nitrophenyl chloroformate or bis-(4-nitrophenyl)carbonate in the presence of a base (such as DIPEA or NMM) yields the corresponding 4-nitrophenyl carbonate derivative (III). In the subsequent step, the activated carbonate (III) is treated with the appropriate piperidine or piperazine derivative (IV) in the presence of a base (such as DIPEA), resulting in the formation of the desired compound of formula (I). This synthesis is generally depicted in Scheme I below.

Alternatively, the piperidine or piperazine derivative (IV) can be activated by treatment with 4-nitrophenyl chloroformate or bis-(4-nitrophenyl)carbonate in the presence of a base to form the corresponding carbamate derivative. The carbamate intermediate is then treated with the appropriate alcohol moiety (II) in the presence of a base to give the compound of formula (I).

The formation of the urethane is typically a two step process but this may also be performed in a one-pot reaction by formation of the activated intermediate in situ.

Scheme 1. General preparation of carbamate derivatives of formula (I)

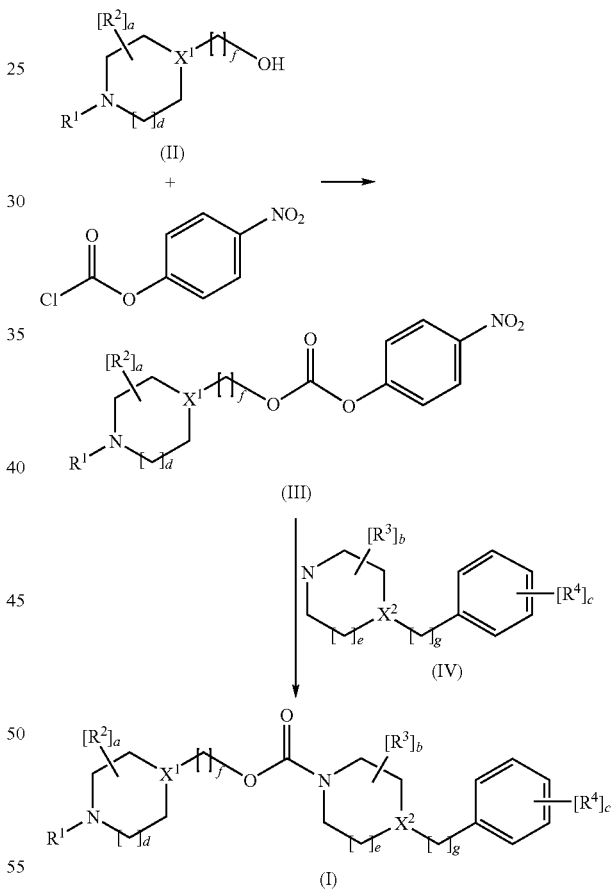

wherein $X^1$, $X^2$, $R^1$-$R^4$ and a-g are as defined in formula I.

The synthesis of amide compounds of formula (I) is typically performed by acylation of a piperidine or piperazine derivative of formula (IV) with the appropriate ω-halo alkanoic acid chloride of formula (V) in the presence of a base (such as DIPEA) to give an amide of formula (VI). Subsequent treatment of (VI) with the appropriate piperazine derivative (VII) in a suitable solvent (such as N-methylpyrrolidinone) yields the desired compound of formula (I). This synthesis is generally depicted in Scheme 2 below.

If necessary, a compound of formula (I) can be transformed into another compound of formula (I) in one or several additional steps.

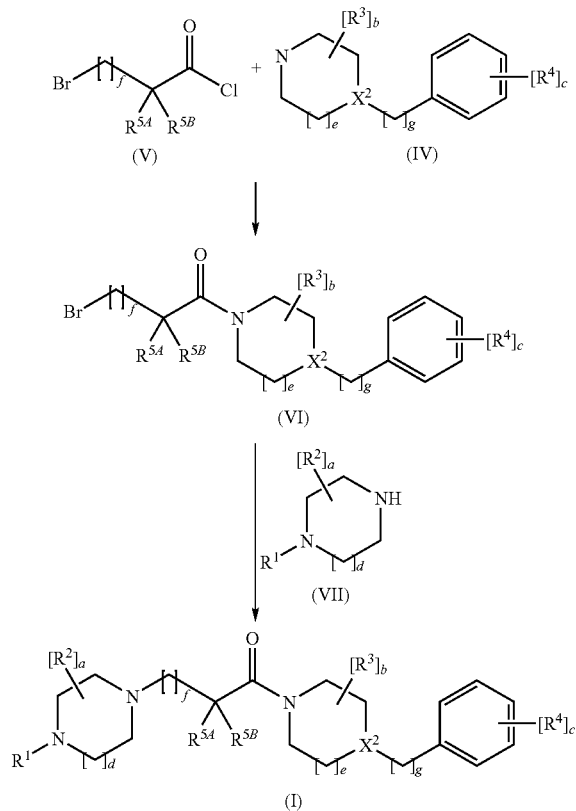

Scheme 2. General preparation of amide derivatives of formula (I)

wherein $X^2$, $R^1$-$R^4$ and a-g are as defined in formula I.

The necessary starting materials for preparing the compounds of formula (I) are either commercially available, or may be prepared by methods known in the art.

The processes described below in the experimental section may be carried out to give a compound in the form of a free base or as an acid addition salt. A pharmaceutically acceptable acid addition salt may be obtained by dissolving the free base in a suitable organic solvent and treating the solution with an acid, in accordance with conventional procedures for preparing acid addition salts from base compounds. Examples of addition salt forming acids are mentioned above.

The compounds of formula (I) may possess one or more chiral carbon atoms, and they may therefore be obtained in the form of optical isomers, e.g., as a pure enantiomer, or as a mixture of enantiomers (racemate) or as a mixture containing diastereomers. The separation of mixtures of optical isomers to obtain pure enantiomers is well known in the art and may, for example, be achieved by fractional crystallization of salts with optically active (chiral) acids or by chromatographic separation on chiral columns.

The chemicals used in the synthetic routes delineated herein may include, for example, solvents, reagents, catalysts, and protecting group and deprotecting group reagents. Examples of protecting groups are t-butoxycarbonyl (Boc), benzyl and trityl (triphenylmethyl). The methods described above may also additionally include steps, either before or after the steps described specifically herein, to add or remove suitable protecting groups in order to ultimately allow synthesis of the compounds. In addition, various synthetic steps may be performed in an alternate sequence or order to give the desired compounds. Synthetic chemistry transformations and protecting group methodologies (protection and deprotection) useful in synthesizing applicable compounds are known in the art and include, for example, those described in R. Larock, Comprehensive Organic Transformations, VCH Publishers (1989); T. W. Greene and P. G. M. Wuts, Protective Groups in Organic Synthesis, 3rd Ed., John Wiley and Sons (1999); L. Fieser and M. Fieser, Fieser and Fieser's Reagents for Organic Synthesis, John Wiley and Sons (1994); and L. Paquette, ed., Encyclopedia of Reagents for Organic Synthesis, John Wiley and Sons (1995) and subsequent editions thereof.

The following abbreviations have been used:
Boc tert-Butoxy carbonyl
DCM Dichloromethane
DIPEA N,N-Diisopropylethylamine
DMAP N,N-Dimethylaminopyridine
DMF N,N-Dimethylformamide
ES+ Electrospray
$Et_2O$ Diethyl ether
EtOAc Ethyl acetate
HIV Human immunodeficiency virus
HPLC High performance liquid chromatography
ICV Intracerebroventricular
LCMS Liquid Chromatography Mass Spectrometry
M Molar
[MH]+ Protonated molecular ion
$NEt_3$ Triethylamine
NMM N-methyl morpholine
RP Reverse Phase
tert Tertiary
TFA Trifluoroacetic acid
THF Tetrahydro furan Embodiments of the disclosure are described in the following examples with reference to the accompanying drawings, in which:

Figure 1:
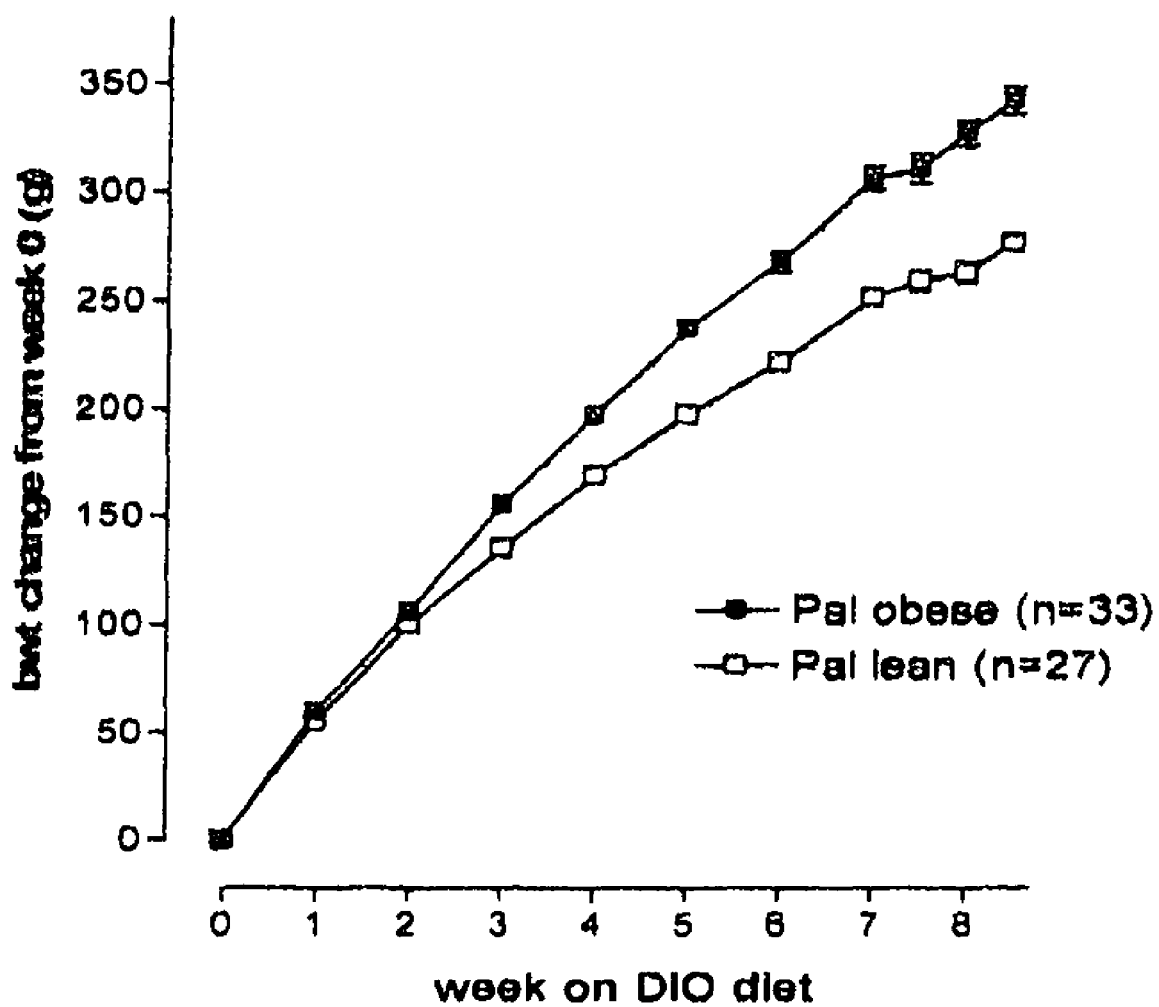
FIG. 1 shows an example of body weight separation between animals fed on a high carbohydrate diet. The error bars represent mean +/−SEM.
Figure 2:
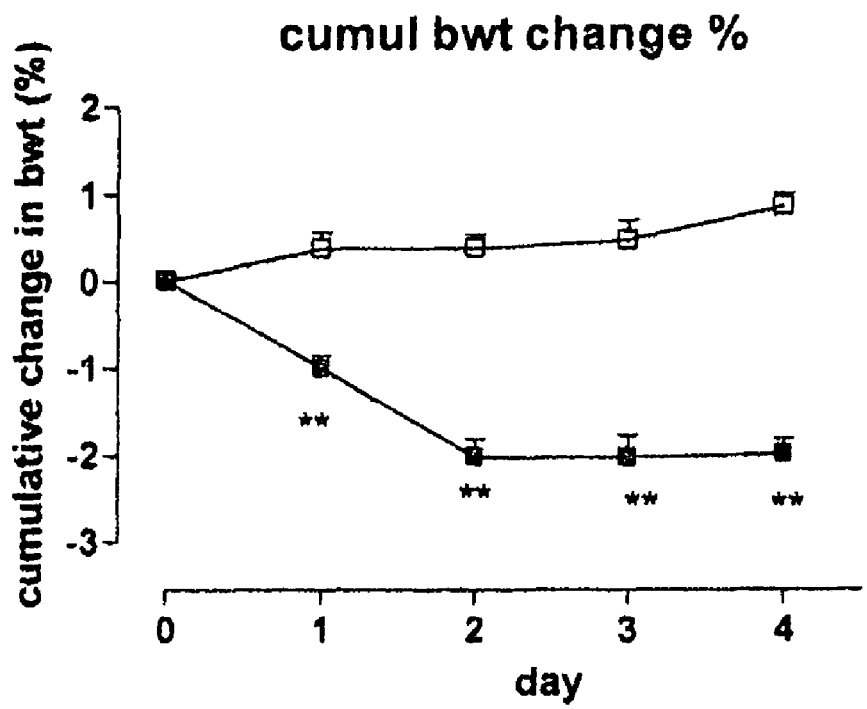
FIG. 2 shows the cumulative body weight change (%) observed in a 4 day study in DIO rats for Example 6.
Figure 3:
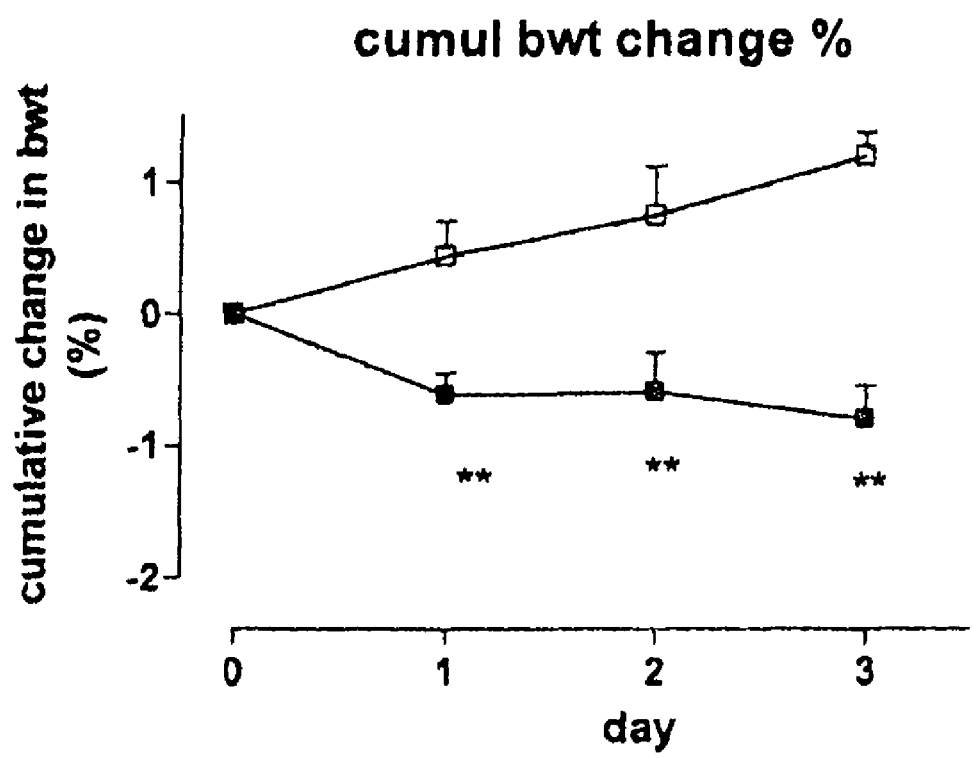
FIG. 3 shows the cumulative body weight change (%) observed in a 3 day study in DIO rats for Example 16.
Figure 4:
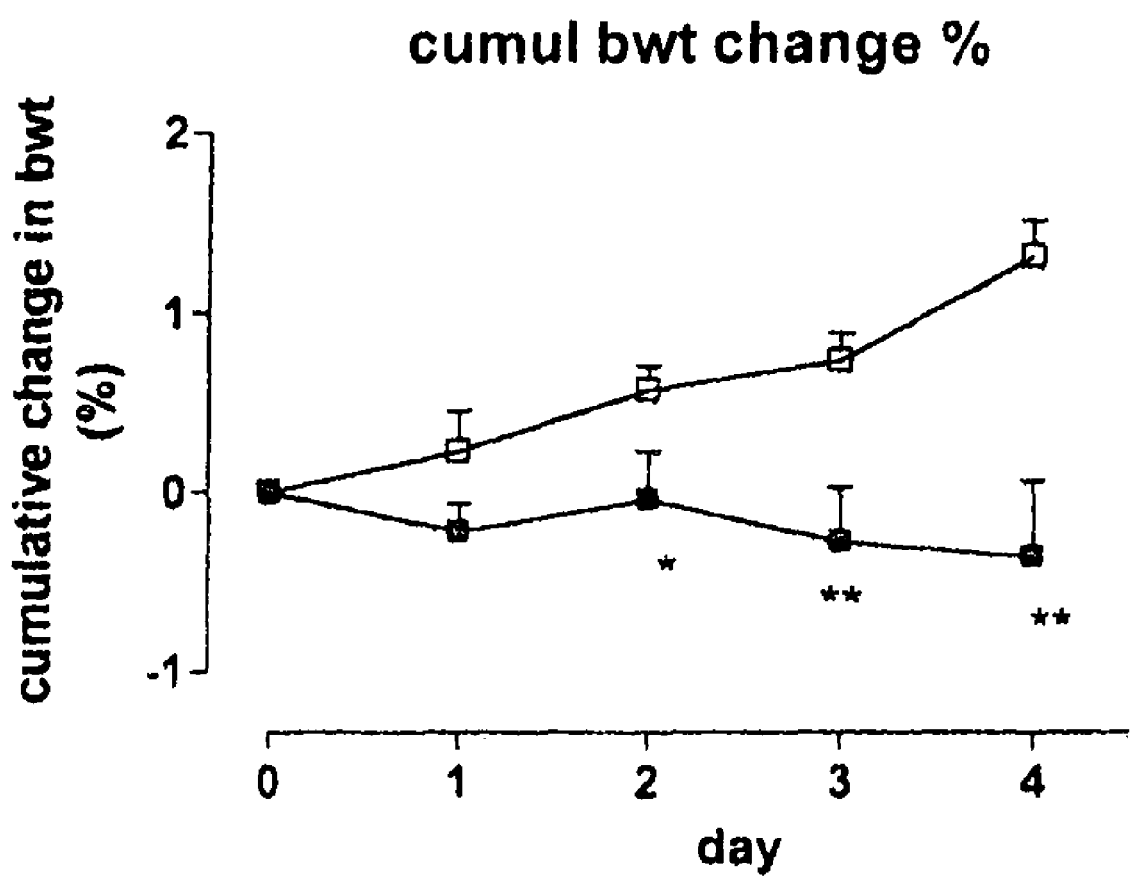
FIG. 4 shows the cumulative body weight change (%) observed in a 4 day study in DIO rats for Example 18.
Figure 5:
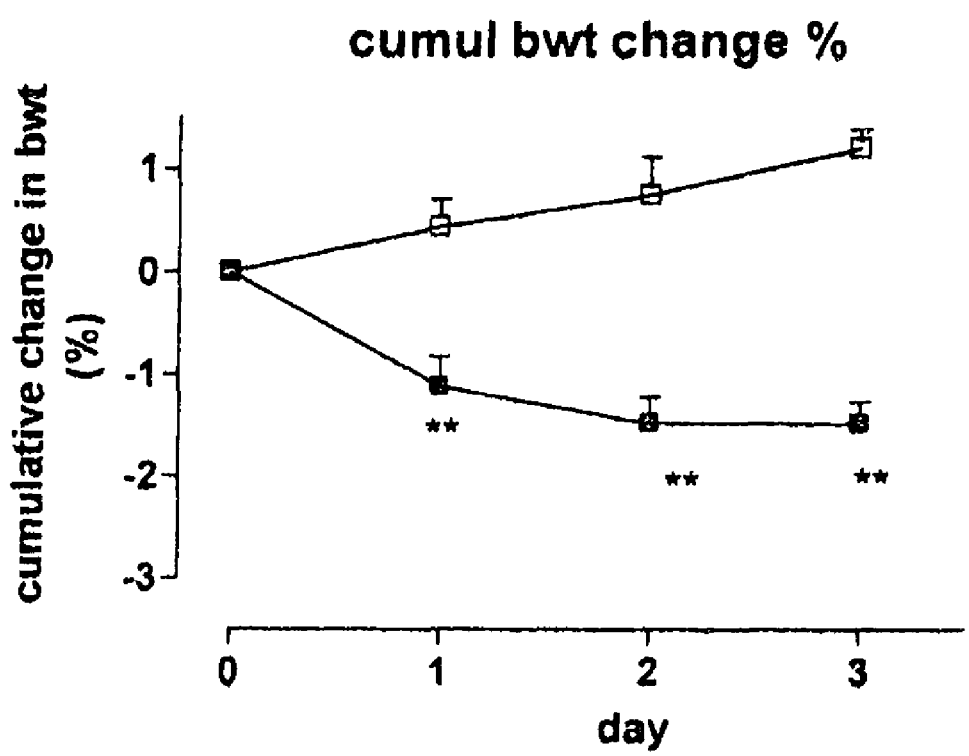
FIG. 5 shows the cumulative body weight change (%) observed in a 3 day study in DIO rats for Example 36.

The recitation of a listing of chemical groups in any definition of a variable herein includes definitions of that variable as any single group or combination of listed groups. The recitation of an embodiment herein includes that embodiment as any single embodiment or in combination with any other embodiments or portions thereof.

The disclosure will now be further illustrated by the following non-limiting examples. The specific examples below are to be construed as merely illustrative, and not limitative of the remainder of the disclosure in any way whatsoever. Without further elaboration, it is believed that one skilled in the art can, based on the description herein, utilize the present disclosure to its fullest extent. All references and publications cited herein are hereby incorporated by reference in their entirety.

EXAMPLES AND INTERMEDIATE COMPOUNDS

Experimental Methods

All reagents were commercial grade and were used as received without further purification, unless otherwise specified. Commercially available anhydrous solvents were used for reactions conducted under inert atmosphere. Reagent grade solvents were used in all other cases, unless otherwise specified. The methyl isocyanate resin was supplied by Nova-Biochem (Cat. No. 01-64-0169). Analytical LCMS was performed on a Waters ZQ mass spectrometer connected to an Agilent 1100 HPLC system. Analytical HPLC was performed on an Agilent 1100 system. High-resolution mass spectra (HRMS) were obtained on an Agilent MSD-TOF connected to an Agilent 1100 HPLC system. During the analyses the calibration was checked by two masses and automatically corrected when needed. Spectra are acquired in positive electrospray mode. The acquired mass range was m/z 100-1100. Profile detection of the mass peaks was used. Flash chromatography was performed on a Flash Master Personal system equipped with Strata SI-1 silica gigatubes. Reverse phase chromatography was performed on a Gilson system equipped with Merck LiChoprep® RP-18 (40-63 µm) 460× 26 mm column, 30 mL/min, gradient of methanol in water. Preparative HPLC was performed on a Gilson system equipped with Phenomenex Hydro RP 150×20 mm, 20 mL/min, gradient of acetonitrile in water. The compounds were automatically named using ACD 6.0 or 8.0.

Analytical HPLC and LCMS data were obtained with:
System A: Phenomenex Synergi Hydro RP, (150×4.6 mm, 4 µm), gradient 5-100% $CH_3CN$ (+0.085% TFA) in $H_2O$ (+0.1% TFA), 1.5 mL/min, with a gradient time of 7 min, 200-300 nm, 30° C.

Analytical LCMS data were also obtained with:
System B: Phenomenex Synergi Hydro RP (150×4.6 mm, 4 µm), gradient 0-20% $CH_3CN$ (+0.1% $HCO_2H$) in $H_2O$ (+0.1% $HCO_2H$), 1 mL/min, gradient time 8 min, 25° C.;
System C: Phenomenex Synergi Hydro RP (30×4.6 mm, 4 µm), gradient 5-100% $CH_3CN$ (+0.085% TFA) in $H_2O$ (+0.1% TFA), 1.5 mL/min, gradient time 1.75 min, 30° C.; or
System D: Phenomenex Synergi Hydro RP (30×4.6 mm, 4 µm), gradient 5-100% $CH_3CN$ (0.1% $HCO_2H$) in $H_2O$ (+0.1% $HCO_2H$), 1.5 mL/min, gradient time 1.75 minutes, 30° C.

Intermediate 1

(1-Methylpiperidin-4-yl)methyl 4-nitrophenyl carbonate

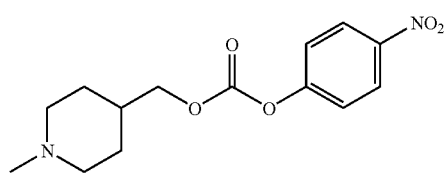

4-Piperidine methanol (10.0 g, 86.8 mmol) was dissolved in DCM (200 mL). DIPEA (15.0 mL, 86.6 mmol) was added before di-tert-butyl dicarbonate (18.95 g, 86.8 mmol) was added portion-wise. The reaction mixture was stirred at room temperature for 19 hours. The reaction mixture was washed with 2M aq HCl (150 mL) and 1 M aq $Na_2CO_3$ (150 mL) and then dried ($MgSO_4$). The resulting organic phase was concentrated in vacuo to give tert-butyl 4-(hydroxymethyl)piperidine-1-carboxylate (16.1 g, 87%) as a white solid.

Analytical LCMS: (System D, $R_T$=1.8 min), $ES^+$: 216.3 $[MH]^+$.

A solution of tert-butyl 4-(hydroxymethyl)piperidine-1-carboxylate (1.94 g, 9.0 mmol) in THF (15.0 mL) was added drop-wise to a 1M solution of $LiAlH_4$ in THF (13.5 mL, 13.5 mmol) under argon. The reaction mixture was stirred at room temperature for 17 hours and then cooled to 0° C. A mixture of THF and water (1:1 ratio, 1.5 mL) was added drop-wise. A gelatinous white solid formed. 4M aq NaOH solution (0.6 mL) was added drop-wise. Water (2 mL) was added and the resulting mixture stirred at room temperature for 2 hours. The white solid was removed by filtration. The filtrate was loaded onto an Isolute HM-N liquid-liquid extraction column and then eluted with EtOAc (200 mL). The resulting organic phase concentrated in vacuo yielding (1-methylpiperidin-4-yl)methanol as a yellow oil (1.02 g, 88%).

Analytical LCMS: purity ~90% (System B, $R_T$=1.88 min), $ES^+$: 129.8 $[MH]^+$.

(1-Methylpiperidin-4-yl)methanol (2.50 g, 19.3 mmol) in DCM (50 mL) was added to a solution of bis-(4-nitrophenyl) carbonate (7.06 g, 23.2 mmol) in DCM (100 mL), followed by NMM (1.70 mL, 15.5 mmol). The reaction mixture was stirred for 90 hours and then washed sequentially with aliquots of 1 M aq $Na_2CO_3$ solution until the aqueous layer was colourless. The organic layer was dried ($MgSO_4$) and concentrated in vacuo to give (1-methylpiperidin-4-yl)methyl 4-nitrophenyl carbonate (4.18 g, 73%) as a yellow solid.

Analytical LCMS: (System D, $R_T$=1.59 min), $ES^+$: 295.1 $[MH]^+$.

Intermediate 2

(1-(tert-Butoxycarbonyl)piperidin-4-yl)methyl 4-nitrophenyl carbonate

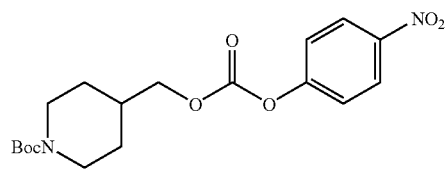

To a solution of tert-butyl 4-(hydroxymethyl)piperidine-1-carboxylate (36.1 g, 168 mmol) and NMM (20 mL, 182 mmol) in DCM (500 mL) at 0° C. was added p-nitrophenyl chloroformate (33.9 g, 168 mmol). The reaction mixture was stirred at room temperature overnight and then washed sequentially with 1M aq HCl (500 mL), sat aq $NaHCO_3$ solution (3×500 mL), dried ($MgSO_4$) and concentrated in vacuo to give (1-(tert-butoxy-carbonyl)piperidin-4-yl)methyl 4-nitrophenyl carbonate (61.2 g, 96%) as a yellow solid.

Analytical LCMS: (System C, $R_T$=2.46 min), ES$^+$: 307.4 [M-O$^t$Bu]$^+$, 281.4 [M+H-Boc]$^+$.

Intermediate 3

(1-(2-Methoxyethyl)piperidin-4-yl)methyl 4-nitrophenyl carbonate

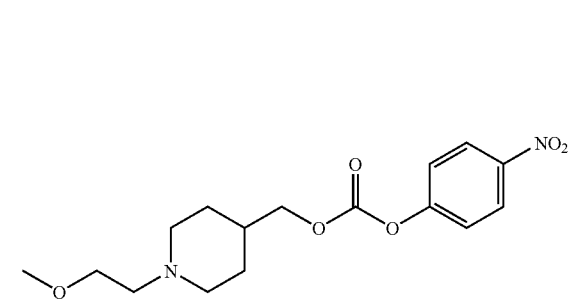

To a solution of piperidin-4-yl-methanol (3.13 g, 27.2 mmol), DMAP (50 mg) and NEt$_3$ (7.0 mL, 50.6 mmol) in DCM at 0° C. was added methoxy-acetyl chloride (5.0 mL, 54.8 mmol) in aliquots: of 0.5 mL. The reaction mixture Was stirred for 2 hours and then diluted with DCM (70 mL) and washed sequentially with 1M aq HCl (100 mL) and 1M aq Na$_2$CO$_3$ (100 mL). The organic phase was dried (MgSO$_4$), filtered and concentrated in vacuo to give (1-(2-methoxy-acetyl)piperidin-4-yl)methyl 2-methoxyacetate (6.5 g, 92%) as a yellow oil.

Analytical LCMS: (System D, $R_T$=1.53 min), ES$^+$: 260.3 [MH]$^+$.

A solution of (1-(2-methoxyacetyl)piperidin-4-yl)methyl 2-methoxyacetate from the previous step (6.5 g, 25.1 mmol) in THF (10 mL) was added drop-wise to a 1 M solution of LiAlH$_4$ in THF (55.0 mL, 55.0 mmol) under argon. The reaction mixture was stirred at room temperature for 2 days and then cooled to 0° C. Water (2.0 mL) was added drop-wise. A gelatinous white solid formed. 0.2M aq NaOH solution (2.0 mL) was added drop-wise. Water (5.0 mL) was added and the resulting mixture stirred at room temperature for 3 h. The white solid was removed by filtration. The filtrate was concentrated in vacuo and dried on an Isolute HM-N cartridge (eluting with EtOAc). The resulting organic solution was dried in vacuo to give (1-(2-methoxyethyl)piperidin-4-yl)methanol (3.65 mg, 84%) as a yellow oil.

Analytical LCMS: (System D, $R_T$=0.35 min), ES$^+$: 174.2 [MH]$^+$.

To a solution of (1-(2-methoxyethyl)piperidin-4-yl)methanol (3.65 g, 21.1 mmol) and NMM (2.5 mL, 22.8 mmol) in DCM (100 mL) at 0° C. was added p-nitrophenyl chloroformate. The reaction mixture was stirred at room temperature overnight and then washed sequentially with sat aq NaHCO$_3$ solution (5×100 mL), dried (MgSO$_4$) and concentrated in vacuo. The resulting orange oil was recrystallised from EtOAc and heptane to give (1-(2-methoxyethyl)piperidin-4-yl)methyl 4-nitrophenyl carbonate (3.65 g, 51%) as an orange solid.

Analytical LCMS: (System D, $R_T$=1.59 min), ES$^+$: 339.2 [MH]$^+$.

Intermediate 4

2-(4-Methylpiperazin-1-yl)ethyl 4-nitrophenyl carbonate

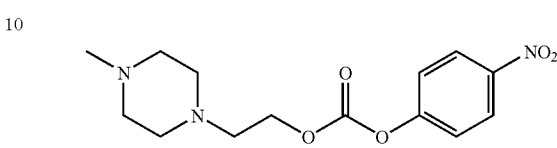

To a stirred solution of 1-(2-hydroxyethyl)piperazine (26.0 g, 0.2 mol) in DMF (200 mL) was added formic acid (752 mL, 0.2 mol) and formaldehyde (16.2 g, 0.2 mol, 37% solution in water) The reaction mixture was cautiously heated at 100° C. for 2 hours then stirred overnight at room temperature. The solvent was removed in vacuo. This procedure was repeated 3 further times to give ~100 g of product. The crude products were combined and distilled under vacuum to give, at 74° C., 2-(4-methylpiperazin-1-yl)ethanol (51 g, 44%) as a colourless liquid. Analytical LCMS: (System C, $R_T$=0.70 min), ES$^+$: 145.1 [MH]$^+$.

4-Nitrophenyl chloroformate (9.85 g, 49 mmol) was dissolved in DCM (200 mL), and cooled to 0° C. 2-(4-methylpiperazin-1-yl)ethanol (7.2 g, 50 mmol) and NMM (6 mL) were added, and the reaction mixture was allowed to warm gradually to room temperature over 16 hours. The reaction mixture was washed with 1M aq Na$_2$CO$_3$ solution until the yellow colour extracted into the aqueous layer had disappeared. The organic phase was dried (MgSO$_4$), filtered and concentrated in vacuo to give 2-(4-methylpiperazin-1-yl) ethyl 4-nitrophenyl carbonate (10.7 g, 71%) as a yellow oil which solidified on standing.

Analytical LCMS: purity ~80% (System C, $R_T$=1.70 min), ES$^+$: 310.4 [MH]$^+$.

Example 1

(1-Methylpiperidin-4-yl)methyl 4-phenylpiperazine-1-carboxylate formate

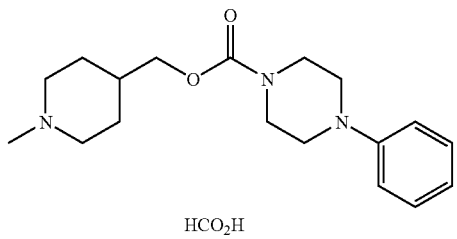

HCO$_2$H (1-Methylpiperidin-4-yl)methyl 4-nitrophenyl carbonate (Intermediate 1; 5.70 g, 19.4 mmol) was dissolved in DMF (40 mL). DIPEA (6.75 mL, 38.7 mmol) and 1-phenyl-piperazine (2.96 mL, 19.4 mmol) were added. The reaction mixture was stirred at room temperature for 6 h and then concentrated in vacuo. The residue was dissolved in EtOAc (300 mL) and washed sequentially with sat aq NaHCO$_3$ solution (6×200 mL), brine (50 mL), dried (MgSO$_4$) and concentrated in vacuo. The residue was purified by normal phase column chromatography (eluting with DCM, followed by a 98:1:1 mixture of DCM:MeOH:DIPEA) followed by reverse phase chromatography (gradient eluting with MeOH in water, with 1% formic acid in each solvent, 0-80%) to give (1-methylpiperidin-4-yl)methyl 4-phenylpiperazine-1-carboxylate formate (0.63 g, 10.3%) as a viscous yellow oil.

Analytical HPLC: purity 100% (System A, $R_T$=3.64 min); Analytical LCMS: purity 100% (System A, $R_T$=4.55 min), ES$^+$: 318.5 [MH]$^+$; HRMS calcd for $C_{18}H_{27}N_3O_2$: 317.2103, found 317.2109.

Example 2

(1-Methylpiperidin-4-yl)methyl 4-(4-chlorophenyl)piperazine-1-carboxylate

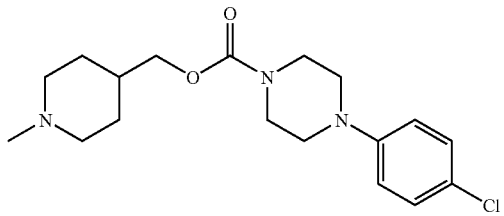

(1-(tert-Butoxycarbonyl)piperidin-4-yl)methyl 4-nitrophenyl carbonate (Intermediate 2; 10.0 g, 26.3 mmol), was dissolved in DMF (50 mL). DIPEA (16.0 mL, 92.0 mmol) and 4-(4-chlorophenyl)piperazine dihydrochloride (7.09 g, 26.3 mmol) were added and the reaction mixture was stirred at room temperature for 24 hours, and the reaction mixture was then concentrated in vacuo. The resulting residue was dissolved in EtOAc (300 mL) and washed with a 1 M aq $Na_2CO_3$ solution (6×200 mL), 10% citric acid solution (50 mL), brine (50 mL), dried ($MgSO_4$) and concentrated in vacuo. The residue was dissolved in a mixture of DCM (100 mL) and TFA (20 mL), stirred for 4 hours and then concentrated in vacuo. The residue was dissolved in 1 M aq $Na_2CO_3$ solution (220 mL), and extracted with DCM (3×200 mL). The combined organic layers were washed with brine (50 mL), dried ($MgSO_4$) and concentrated in vacuo. The residue was recrystallised from EtOAc to give (1-piperidin-4-yl)methyl 4-(4-chlorophenyl)piperazine-1-carboxylate (4.07 g, 45.7%) as a cream solid.

Analytical LCMS: purity 100% (System C, $R_T$=1.94 min), ES$^+$: 338.4 [MH]$^+$.

(1-piperidin-4-yl)methyl 4-(4-chlorophenyl)piperazine-1-carboxylate (4.07 g, 12.0 mmol) was dissolved in formic acid (20 mL) and 35% aqueous formaldehyde solution (20 mL). The reaction mixture was heated at 95° C. for 90 minutes, and then cooled to room temperature. The reaction mixture was quenched by slowly pouring it onto 1M aq $Na_2CO_3$ solution (200 mL), basified to pH10 with 1M aq KOH solution (30 mL) and extracted with DCM (3×100 mL). The combined organic layers were washed with brine (50 mL), dried ($MgSO_4$) and concentrated in vacuo. The residue was purified by normal phase column chromatography (eluting with DCM, followed by a 97:2:1 mixture of DCM:MeOH:DIPEA) followed by reverse phase column chromatography (gradient eluting with MeOH in water, 0-80%) to give (1-methylpiperidin-4-yl)methyl 4-(4-chlorophenyl)piperazine-1-carboxylate (1.30 g, 30.7%) as a white solid.

Analytical HPLC: purity 99.8% (System A, $R_T$=4.75 min); Analytical LCMS: purity 100% (System A, $R_T$=6.43 min), ES$^+$: 352.4 [MH]$^+$; HRMS calcd for $C_{18}H_{26}ClN_3O_2$: 351.1714, found 351.1729.

Example 3

Piperidin-4-ylmethyl 4-(4-methylphenyl)piperazine-1-carboxylate

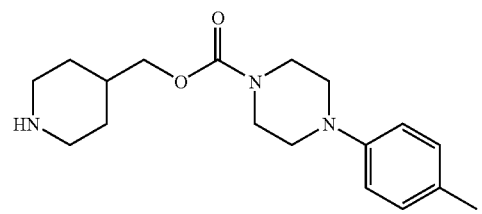

(tert-Butoxycarbonyl)piperidin-4-ylmethyl 4-nitrophenyl carbonate (Intermediate 2; 3.80 g, 10.0 mmol) was dissolved in DMF (100 mL). DIPEA (6.10 mL, 35.0 mmol) and 4-(4-methylphenyl)piperazine dihydrochloride (2.49 g, 10.0 mmol) were added. The reaction mixture was stirred at room temperature for 4 hours and then concentrated in vacuo. The resulting residue was dissolved in EtOAc (300 mL) and washed with a 1 M aq $Na_2CO_3$ solution (6×200 mL), 10% citric acid solution (50 mL), brine (50 mL), dried ($MgSO_4$) and concentrated in vacuo. The residue was dissolved in a mixture of DCM (100 mL) and TFA (25 mL), stirred for 48 hours and then concentrated in vacuo. The residue was purified by reverse phase column chromatography (gradient eluting with MeOH in water, with 1% formic acid in each solvent, 0-30%). The resulting residue was dissolved in DCM (70 mL) and stirred with solid $K_2CO_3$ for 20 minutes, filtered and concentrated in vacuo to give piperidin-4-ylmethyl 4-(4-methylphenyl)piperazine-1-carboxylate (1.60 g, 44.6%) as a pale yellow solid.

Analytical HPLC: purity 99.8% (System A, $R_T$=3.71 min); Analytical LCMS: purity 100% (System A, $R_T$=4.32 min), ES$^+$: 318.2 [MH]$^+$; HRMS calcd for $C_{18}H_{27}N_3O_2$: 317.2103, found 317.2106.

Example 4

(1-Methylpiperidin-4-yl)methyl 4-(4-methylphenyl)piperazine-1-carboxylate

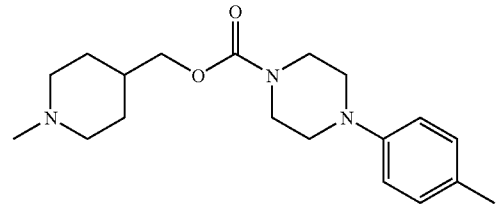

(1-piperidin-4-yl)methyl 4-(4-methylphenyl)piperazine-1-carboxylate (Example 3; 9.75 g, 30.7 mmol) was dissolved in formic acid (3 mL), 35% aqueous formaldehyde solution (3 mL) and water (20 mL). The reaction mixture was heated at 95° C. for 45 minutes, and then cooled to room temperature.

The reaction mixture was quenched by slowly pouring it onto 1M aq Na$_2$CO$_3$ solution (400 mL) and extracted with EtOAc (4×150 mL). The combined organic layers were washed with brine (75 mL), dried (MgSO$_4$) and concentrated in vacuo. The residue was recrystallised from heptane and then purified by reverse phase column chromatography (gradient eluting with MeOH in water, with 1% formic acid in each solvent, 0-30%). The resulting residue was dissolved in DCM (70 mL) and stirred with solid K$_2$CO$_3$ for 20 minutes, filtered and concentrated in vacuo. The residue was recrystallised from heptane to give (1-methylpiperidin-4-yl)methyl 4-(4-methylphenyl)-piperazine-1-carboxylate (4.38 g, 43.0%) as a white solid.

Analytical HPLC: purity 100% (System A, R-r=3.67 min); Analytical LCMS: purity 100% (System A, R$_T$=5.37 min), ES$^+$: 332.5 [MH]$^+$; HRMS calcd for C$_{19}$H$_{29}$N$_3$O$_2$: 331.2260, found 331.2274.

Example 5

(1-Methylpiperidin-4-yl)methyl 4-(3-methylphenyl)piperazine-1-carboxylate

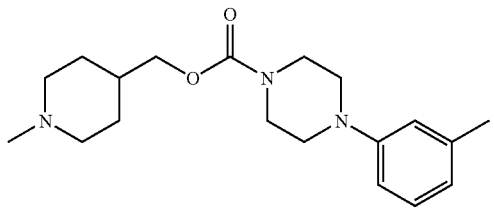

(1-Methylpiperidin-4-yl)methyl 4-nitrophenyl carbonate (Intermediate 1; 4.30 g, 14.6 mmol) was dissolved in DMF (50 mL). DIPEA (8.91 mL, 51.1 mmol) and 4-(3-methylphenyl)piperazine dihydrochloride (3.64 g, 14.6 mmol) were added. The reaction mixture was stirred at room temperature for 4 hours and then concentrated in vacuo. The residue was dissolved in EtOAc (500 mL) and then washed sequentially with 1 M aq NaOH solution (6×200 mL), brine (50 mL), dried (MgSO$_4$) and concentrated in vacuo. The residue was dissolved in DCM (150 mL) and methyl isocyanate resin (1.0 g) was added and the reaction mixture shaken for 14 h, filtered and then concentrated in vacuo. The residue was purified by reverse phase chromatography (gradient eluting with MeOH in water, with 1% formic acid in each solvent, 0-30%). The resulting residue was dissolved in DCM (70 mL) and stirred with solid K$_2$CO$_3$ for 20 minutes, filtered and concentrated in vacuo to give (1-methylpiperidin-4-yl)methyl 4-(3-methylphenyl)piperazine-1-carboxylate (0.65 g, 13.3%) as a pale yellow oil.

Analytical HPLC: purity 100% (System A, R$_T$=3.84 min); Analytical LCMS: purity 100% (System A, R$_T$=5.63 min), ES$^+$: 332.4 [MH]$^+$; HRMS calcd for C$_{19}$H$_{29}$N$_3$O$_2$: 331.2260, found 331.2272.

Example 6

(1-Methylpiperidin-4-yl)methyl 4-(4-fluorophenyl)piperazine-1-carboxylate

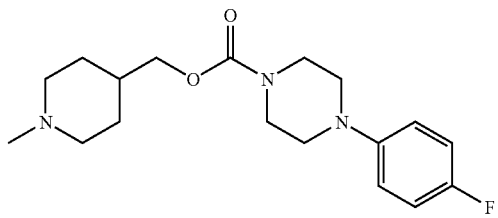

(1-Methylpiperidin-4-yl)methyl 4-nitrophenyl carbonate (Intermediate 1; 4.99 g, 16.9 mmol) was dissolved in DMF (40 mL). DIPEA (5.90 mL, 33.9 mmol) and 4-(4-fluorophenyl)piperazine (3.21 g, 17.8 mmol) were added. The reaction mixture was stirred at room temperature for 3 h and then concentrated in vacuo. The residue was dissolved in EtOAc (400 mL) and then washed sequentially with 1 M aq NaOH solution (6×150 mL), brine (50 mL), dried (MgSO$_4$) and concentrated in vacuo. The residue was dissolved in DCM (100 mL) and methyl isocyanate resin (1.0 g) was added. The reaction mixture was shaken for 14 h, filtered and then concentrated in vacuo. The residue was purified by reverse phase chromatography (gradient eluting with MeOH in water, with 1% formic acid in each solvent, 0-30%). The resulting residue was dissolved in DCM (70 mL) and stirred with solid K$_2$CO$_3$ for 20 minutes, filtered and concentrated in vacuo to give (1-methylpiperidin-4-yl)methyl 4-(4-fluorophenyl)piperazine-1-carboxylate (0.67 g, 11.8%) as a pale yellow oil.

Analytical HPLC: purity 98.9% (System A, R$_T$=4.09 min); Analytical LCMS: purity 97.0% (System A, R$_T$=4.65 min), ES$^+$: 336.1 [MH]$^+$; HRMS calcd for C$_{19}$H$_{26}$FN$_3$O$_2$: 335.2009, found 335.2022.

Example 7

(1-Methylpiperidin-4-yl)methyl 4-(4-methoxyphenyl)piperazine-1-carboxylate

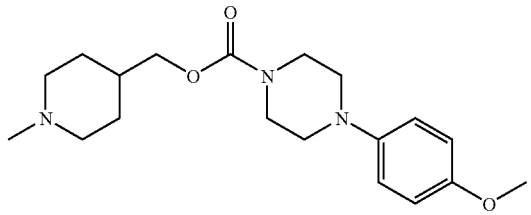

(1-Methylpiperidin-4-yl)methanol (1.00 g, 7.74 mmol) was dissolved in DCM (20 mL) and cooled to 0° C. NMM (0.94 mL, 8.51 mmol) and 4-nitrophenyl chloroformate (1.56 g, 7.74 mmol) were added. The reaction mixture was stirred at 0° C. for 20 minutes and then added to a solution of 4-(4-methoxyphenyl)piperazine (1.64 g, 8.51 mmol) and DIPEA (2.02 mL, 11.01 mmol) in DMF (30 mL). The reaction mixture was stirred at room temperature for 4 h and then concentrated in vacuo. The residue was dissolved in EtOAc (200 mL) and washed sequentially with 1 M aq NaOH solution (5×100 mL), brine (100 mL), dried (MgSO$_4$) and concentrated in vacuo. The residue was purified by reverse phase chromatography (gradient eluting with MeOH in water, with 1% formic acid in each solvent, 0-30%). The resulting residue was dissolved in DCM (70 mL) and stirred with solid K$_2$CO$_3$ for 20 minutes, filtered and concentrated in vacuo to give (1-methylpiperidin-4-yl)methyl 4-(4-methoxyphenyl)piperazine-1-carboxylate (0.277 g, 10.3%) as an off-white solid.

Analytical HPLC: purity 99.2% (System A, R$_T$=3.51 min); Analytical LCMS: purity 97.3% (System A, R$_T$=4.09 min), ES$^+$: 348.5 [MH]$^+$; HRMS calcd for C$_{19}$H$_{29}$N$_3$O$_3$: 347.2209, found 347.2222.

Example 8

[1-(2-Methoxyethyl)piperidin-4-yl]methyl 4-phenylpiperazine-1-carboxylate

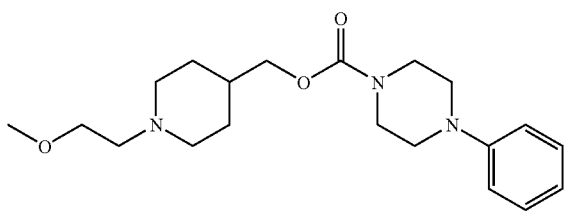

(1-(tert-Butoxycarbonyl)piperidin-4-yl)methyl 4-nitrophenyl carbonate (Intermediate 2; 5.0 g, 13.1 mmol) was dissolved in DMF (30 mL). DIPEA (4.58 mL, 26.3 mmol) and 1-phenylpiperazine (2.01 mL, 13.1 mmol) were added. The reaction mixture was stirred at room temperature for 18 h and then concentrated in vacuo. The residue was dissolved in EtOAc (300 mL) and then washed sequentially with sat aq NaHCO$_3$ solution (6×200 mL), 10% citric acid solution (50 mL) and brine (50 mL). The solution was dried (MgSO$_4$) and concentrated in vacuo. The residue was dissolved in DCM (20 mL) and TFA (10 mL) was added. The reaction mixture was stirred at room temperature for 3 hours and then concentrated in vacuo. The residue was dissolved in water (20 mL), sat aq NaHCO$_3$ solution (100 mL) was added and the aqueous layer was extracted with DCM (3×200 mL). The combined organic layers were then washed with brine (50 mL), dried (MgSO$_4$) and the solution was concentrated in vacuo to give (piperidin-4-yl)methyl 4-phenylpiperazine-1-carboxylate (3.825 g, 95.9% yield) as a yellow solid.

Analytical LCMS: (System C, R$_T$=1.64 min), ES$^+$: 304.4 [MH]$^+$.

(Piperidin-4-yl)methyl 4-phenylpiperazine-1-carboxylate from the previous step (2.15 g, 7.10 mmol), 2-bromoethylmethylether (0.67 mL, 7.10 mmol) and DIPEA (1.36 mL, 7.81 mmol) were dissolved in DMF (30 mL) and stirred overnight at 70° C. and then concentrated in vacuo. The residue was dissolved in DCM (300 mL) and then washed sequentially with sat aq NaHCO$_3$ solution (2×100 mL), brine (50 mL), dried (MgSO$_4$) and concentrated in vacuo. The residue was purified by normal phase column chromatography (eluting with DCM, followed by a 98:1:1 mixture of DCM:MeOH: DIPEA) followed by reverse phase chromatography (gradient eluting with MeOH in water, 0-100%) to give the title compound [1-(2-methoxyethyl)piperidin-4-yl]methyl 4-phenylpiperazine-1-carboxylate (0.798 g, 31.1% yield) as a viscous yellow oil.

Analytical HPLC: purity 99.9% (System A, R$_T$=3.83 min); Analytical LCMS: purity 100% (System A, R$_T$=4.59 min), ES$^+$: 362.5 [MH]$^+$; HRMS calcd for C$_{20}$H$_{31}$N$_3$O$_3$: 361.2365, found 361.2382.

Example 9

[1-(2-Methoxyethyl)piperidin-4-yl]methyl 4-(4-fluorophenyl)piperazine-1-carboxylate dihydrochloride

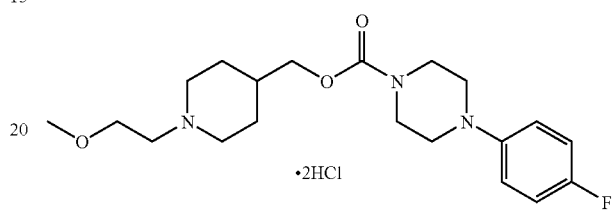

(1-(2-Methoxyethyl)piperidin-4-yl)methyl 4-nitrophenyl carbonate (Intermediate 3; 1.01 g, 3.0 mmol) was dissolved in DMF (10 mL). DIPEA (0.87 mL, 5.0 mmol) and 4-(4-fluorophenyl)piperazine (541 mg, 3.0 mmol) were added and the reaction mixture was stirred at room temperature for 14 hours, and the reaction mixture was then concentrated in vacuo. The resulting residue was dissolved in EtOAc (50 mL) and washed with a 1 M aq Na$_2$CO$_3$ solution (5×30 mL), dried (MgSO$_4$) and concentrated in vacuo. The residue was purified by normal phase column chromatography (eluting with DCM, followed by a 96:4 mixture of DCM:MeOH) followed by reverse phase column chromatography (gradient eluting with MeOH in water, 0-100%). The residue was dissolved in DCM (10 mL) and 2M HCl in Et$_2$O (3 mL) was added. The reaction mixture was then concentrated in vacuo to give [1-(2-methoxyethyl)piperidin-4-yl]methyl 4-(4-fluorophenyl)piperazine-1-carboxylate dihydrochloride (90 mg, 7.9%) as white solid.

Analytical HPLC: purity 99.3% (System A, R$_T$=4.25 min); Analytical LCMS: purity 100% (System A, R$_T$=5.80 min), ES$^+$: 380.5 [MH]$^+$; HRMS calcd for C$_{20}$H$_{30}$FN$_3$O$_3$: 379.2271, found 379.2281.

Example 10

[1-(2-Methoxyethyl)piperidin-4-yl]methyl 4-(4-chlorophenyl)piperazine-1-carboxylate dihydrochloride

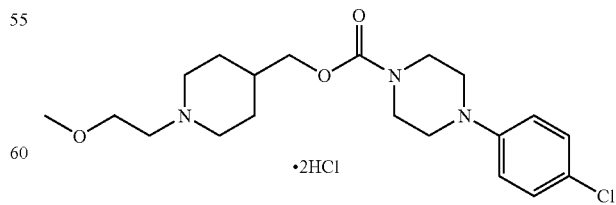

(1-(2-methoxyethyl)piperidin-4-yl)methyl 4-nitrophenyl carbonate (Intermediate 3; 1.01 g, 3.0 mmol) was dissolved in DMF (10 mL). DIPEA (1.74 mL, 5.0 mmol) and, 4-(4-chlorophenyl)piperazine dihydrochloride (808 mg, 3.0 mmol)

were added and the reaction mixture was stirred at room temperature for 14 hours, and the reaction mixture was then concentrated in vacuo. The resulting residue was dissolved in EtOAc (50 mL) and washed with 1M aq Na$_2$CO$_3$ solution (5×30 mL), dried (MgSO$_4$) and concentrated in vacuo. The residue was purified by normal phase column chromatography (eluting with DCM, followed by a 96:4 mixture of DCM: MeOH) followed by reverse phase column chromatography (gradient eluting with MeOH in water, 0-100%). The residue was dissolved in DCM (10 mL) and 2M HCl in Et$_2$O (3 mL) was added. The reaction mixture was then concentrated in vacuo to give [1-(2-methoxyethyl)piperidin-4-yl]methyl 4-(4-chlorophenyl)piperazine-1-carboxylate dihydrochloride (468 mg, 39.5%) as white solid.

Analytical HPLC: purity 99.6% (System A, R$_T$=5.04 min); Analytical LCMS: purity 100% (System A, R$_T$=6.73 min), ES$^+$: 396.5 [MH]$^+$; HRMS calcd for C$_{20}$H$_{30}$ClN$_3$O$_2$: 395.1976 found 395.1994.

Example 11

[1-(2-Methoxyethyl)piperidin-4-yl]methyl 4-(4-methylphenyl)piperazine-1-carboxylate

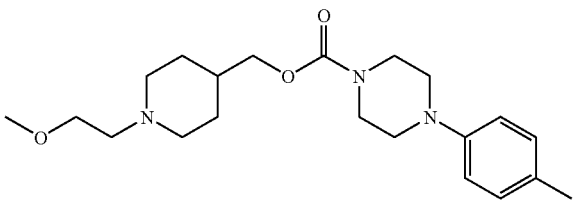

(1-(2-methoxyethyl)piperidin-4-yl)methanol (Intermediate 3, step 2; 1.73 g, 10.0 mmol) was dissolved in DCM (50 mL) and cooled to 0° C. NMM (1.21 mL, 11.0 mmol) and 4-nitrophenyl chloroformate (2.02 g, 10.0 mmol) were added. The reaction mixture was stirred at 0° C. for 15 minutes and then added to a solution of 4-(4-methylphenyl)piperazine dihydrochloride (2.62 g, 10.5 mmol) and DIPEA (6.10 mL, 35.0 mmol) in DMF (75 mL). The reaction mixture was stirred at room temperature for 4 h and then concentrated in vacuo. The residue was dissolved in EtOAc (300 mL) and then washed sequentially with 1M aq NaOH solution (6×100 mL), brine (100 mL), and then dried (MgSO$_4$) and concentrated in vacuo. The residue was purified by reverse phase chromatography (gradient eluting with MeOH in water, with 1% formic acid in each solvent, 0-30%). The resulting residue was dissolved in DCM (70 mL) and stirred with solid K$_2$CO$_3$ for 20 minutes, filtered and concentrated in vacuo to give [1-(2-methoxyethyl)piperidin-4-yl]-methyl 4-(4-methylphenyl)piperazine-1-carboxylate (0.95 g, 25.4%) as a pale yellow oil.

Analytical HPLC: purity 100% (System A, R$_T$=4.08 min); Analytical LCMS: purity 100% (System A, R$_T$=4.70 min), ES$^+$: 376.5 [MH]$^+$; HRMS calcd for C$_{21}$H$_{33}$N$_3$O$_3$: 375.2522, found 375.2534.

Example 12

[1-(2-Methoxyethyl)piperidin-4-yl]methyl 4-(4-methoxyphenyl)piperazine-1-carboxylate

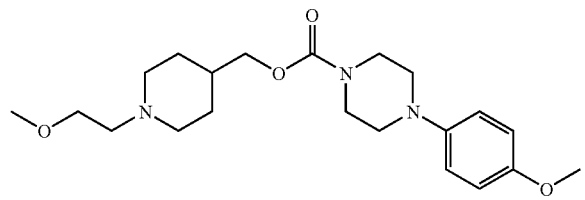

(1-(2-methoxyethyl)piperidin-4-yl)methanol (Intermediate 3, step 2; 1.34 g, 7.74 mmol) was dissolved in DCM (20 mL) and cooled to 0° C. NMM (0.94 mL, 8.51 mmol) and 4-nitrophenyl chloroformate (1.56 g, 7.74 mmol) were added. The reaction mixture was stirred at 0° C. for 20 minutes and then added to a solution of 4-(4-methoxyphenyl)piperazine (1.64 g, 8.51 mmol) and DIPEA (6.10 mL, 35.0 mmol) in DMF (30 mL). The reaction mixture was stirred at room temperature for 4 h and then concentrated in vacuo. The residue was dissolved in EtOAc (300 mL) and then washed sequentially with 1M aq NaOH solution (5×125 mL), brine (100 mL), and then dried (MgSO$_4$) and concentrated in vacuo. The residue was purified by reverse phase chromatography (gradient eluting with MeOH in water, with 1% formic acid in each solvent, 0-30%). The resulting residue was dissolved in DCM (70 mL) and stirred with solid K$_2$CO$_3$ for 20 minutes, filtered and concentrated in vacuo to give the title compound [1-(2-methoxyethyl)piperidin-4-yl]methyl 4-(4-methoxyphenyl)piperazine-1-carboxylate (0.637 g, 21.6%) as a pale yellow oil.

Analytical HPLC: purity 99.9% (System A, R$_T$=4.87 min); Analytical LCMS: purity 100% (System A, R$_T$=4.18 min), ES$^+$: 392.1 [MH]$^+$; HRMS calcd for C$_{21}$H$_{33}$N$_3$O$_4$: 391.2471, found 391.2471

Example 13

2-(1-Methylpiperidin-4-yl)ethyl 4-(4-methylphenyl)piperazine-1-carboxylate

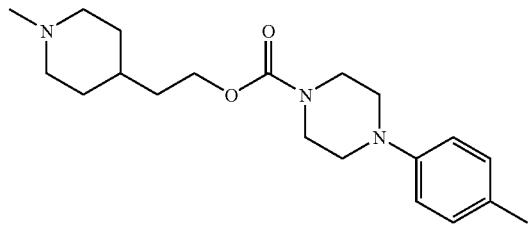

2-Piperidin-4-yl-ethanol (2.37 g, 18.3 mmol) was dissolved in formic acid (2.1 mL, 55.7 mmol), 35% aqueous formaldehyde solution (4.5 mL, 55.4 mmol) and water (20 mL). The reaction mixture was heated at 95° C. for 2 hours, and then cooled to room temperature. The reaction mixture was quenched by slowly pouring it onto a saturated NaHCO$_3$ solution (200 mL) and concentrated in vacuo. The residue was suspended in MeOH (100 mL) and stirred for 2 hours, filtered, and the filtrate was concentrated in vacuo to give 2-(1-methyl-piperidin-4-yl)-ethanol (3.38 g, 129%) as a colourless oil which was used without further purification.

Analytical LCMS: (System C, R$_T$=0.50 min), ES$^+$: 144.1 [MH]$^+$.

NaH (60% dispersion in mineral-oil, 0.81 g, 42.2 mmol) was suspended in heptane (10 mL) under an argon atmosphere. The heptane was decanted off, and the flask was charged with THF (20 mL) and cooled to 0° C. A solution of 2-(1-methyl-piperidin-4-yl)-ethanol (1.01 g, 7.03 mmol) in THF (20 mL) was added drop-wise, followed by a solution of 4-nitrophenyl 4-(4-methylphenyl)piperazine-1-carboxylate (2.89 g, 8.46 mmol) in THF (20 mL). The reaction mixture was allowed to warm to room temperature and stirred for 48 hours. The reaction mixture was then cooled to 0° C. and quenched with the drop-wise addition of sat aq NaHCO$_3$ solution and concentrated in vacuo. The residue was dissolved in EtOAc (200 mL), washed with a NaHCO$_3$ solution (4×50 mL), dried (MgSO$_4$) and concentrated in vacuo. The residue was purified by normal phase column chromatography (eluting with DCM, followed by a 90:10 mixture of DCM:MeOH) followed by reverse phase chromatography (gradient eluting with MeOH in water, with 1% formic acid in each solvent, 0-20%). The resulting residue was dissolved in DCM (50 mL) and stirred with solid K$_2$CO$_3$ for 20 minutes, filtered and concentrated in vacuo to give the title compound 2-(1-methylpiperidin-4-yl)ethyl 4-(4-methylphenyl)piperazine-1-carboxylate (0.21 g, 7%) as a cream solid.

Analytical HPLC: purity 99.6% (System A, R$_T$=4.02 min); Analytical LCMS: purity 100% (System A, R$_T$=4.48 min), ES$^+$: 346.5 [MH]$^+$; HRMS calcd for C$_{20}$H$_{31}$N$_3$O$_2$: 345.2416, found 345.2427

Example 14

1-Methylpiperidin-4-yl 4-(4-methylphenyl)piperazine-1-carboxylate

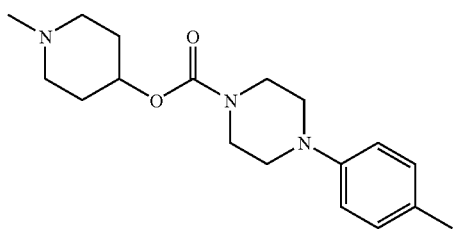

To a solution of 4-hydroxy-1-methyl piperidine (3.00 g, 26.1 mmol) and NMM (3.0 mL, 27.3 mmol) in DCM (50 mL) at 0° C. was added p-nitrophenyl chloroformate (5.51 g, 27.4 mmol). The reaction mixture was stirred at room temperature for 4 hours, and a cream precipitate gradually formed. The reaction mixture was filtered and the residue was washed with DCM (50 mL) to give 1-methylpiperidin-4-yl 4-nitrophenyl carbonate (7.24 g, 99%) as a cream solid.

Analytical LCMS: (System C, R$_T$=2.02 min), ES$^+$: 281.4 [MH].

To a solution of 1-methylpiperidin-4-yl 4-nitrophenyl carbonate (1.81 g, 6.44 mmol) and DIPEA (0.76 mL, 4.4 mmol) in DMF (20 mL) was added 4-(4-methylphenyl)piperazine (1.53 g, 6.14 mmol). The reaction mixture was stirred at room temperature for 3 hours, the reaction mixture was then concentrated in vacuo. The resulting residue was dissolved in EtOAc (250 mL) and washed with 1M aq Na$_2$CO$_3$ (5×150 mL), dried (MgSO$_4$) and concentrated in vacuo. The residue was purified by normal phase column chromatography (eluting with DCM, followed by a 90:10 mixture of DCM:MeOH) to give 1-methyl-piperidin-4-yl 4-(4-methylphenyl)piperazine-1-carboxylate (1.54 g, 79%) as a cream solid.

Analytical HPLC: purity 100% (System A, R$_T$=3.73 min); Analytical LCMS: purity 100% (System A, R$_T$=4.90 min), ES$^+$: 318.5 [MH]$^+$; HRMS calcd for C$_{18}$H$_{27}$N$_3$O$_2$: 317.2103, found 317.2117.

Example 15

[(3S)-1-Methylpyrrolidin-3-yl]-4-(4-methylphenyl) piperazine-1-carboxylate

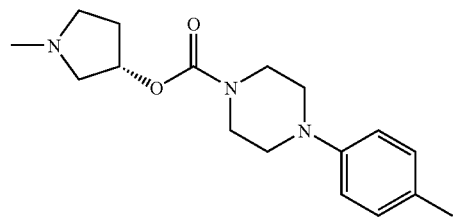

(S)-(+)-3-Hydroxy-N-methylpyrrolidine (1.51 g, 14.9 mmol) was dissolved in DCM (20 mL) and cooled to 0° C. NMM (1.70 mL, 15.5 mmol) and 4-nitrophenyl chloroformate (3.16 g, 15.7 mmol) were added. The reaction mixture was stirred at 0° C. for 30 minutes and then a solution of 4-(4-methylphenyl)piperazine dihydrochloride (3.71 g, 14.9 mmol) and DIPEA (7.40 mL, 44.7 mmol) in DMF (20 mL) was added. The reaction mixture was stirred at room temperature for 3 hours and then concentrated in vacuo. The residue was dissolved in EtOAc (300 mL) and then washed with 1 M aq Na$_2$CO$_3$ solution (5×200 mL), dried (MgSO$_4$) and concentrated in vacuo. The residue was dissolved in DCM (100 mL) and methyl isocyanate resin (2.0 g) was added, the reaction mixture was shaken for 14 h, filtered and then concentrated in vacuo. The residue was purified by reverse phase chromatography (gradient eluting with MeOH in water, with 1% formic acid in each solvent, 0-30%). The resulting residue was dissolved in DCM (70 mL) and stirred with solid K$_2$CO$_3$ for 20 minutes, filtered and concentrated in vacuo. The resulting residue was purified by normal phase column chromatography (eluting with DCM, followed by a 90:10 mixture of DCM:MeOH) to give [(3S)-1-methylpyrrolidin-3-yl]-4-(4-methylphenyl)-piperazine-1-carboxylate (606 mg, 13.0%) as a yellow oil.

Analytical HPLC: purity 99.1% (System A, $R_T$=3.71 min); Analytical LCMS: purity 100% (System A, $R_T$=4.42 min), ES$^+$: 304.1 [MH]$^+$; HRMS calcd for $C_{17}H_{25}N_3O_2$: 303.1947, found 303.1957.

Example 16

2-(4-Methylpiperazin-1-yl)ethyl 4-phenylpiperazine-1-carboxylate formate

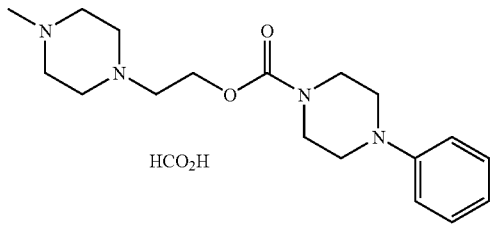

2-(4-Methylpiperazin-1-yl)ethyl 4-nitrophenyl carbonate (Intermediate 4; 1.58 g, 5.1 mmol) was dissolved in DMF (25 mL). DIPEA (0.87 mL, 5.0 mmol) and 4-phenyl-piperazine (807 mg, 0.76 mL, 5.0 mmol) were added and the reaction mixture was stirred at room temperature for 14 hours. The reaction mixture was then concentrated in vacuo. The residue was purified by reverse phase column chromatography (gradient eluting with MeOH in water, with 1% formic acid in each solvent, 0-100%) to give 2-(4-methyl-piperazin-1-yl) ethyl 4-phenylpiperazine-1-carboxylate formate (113 mg, 6.7%) as a yellow oil.

Analytical HPLC: purity 100% (System A, $R_T$=3.40 min); Analytical LCMS: purity 99.2% (System A, $R_T$=5.08 min), ES$^+$: 333.5 [MH]$^+$; HRMS calcd for $C_{18}H_{28}N_4O_2$: 332.2212, found 332.2225

Example 17

2-(4-Methylpiperazin-1-yl)ethyl 4-(4-chlorophenyl) piperazine-1-carboxylate

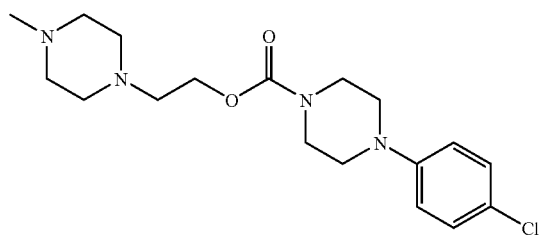

2-(4-Methylpiperazin-1-yl)ethyl 4-nitrophenyl carbonate (Intermediate 4; 740 mg, 2.4 mmol) was dissolved in DMF (20 mL). NEt$_3$ (1.2 mL, 8.6 mmol) and 4-(4-chlorophenyl) piperazine dihydrochloride (691 mg, 2.6 mmol) were added and the reaction mixture was stirred at room temperature for 24 hours, and the reaction mixture was then concentrated in vacuo. The resulting residue was dissolved in EtOAc (50 mL) and washed with 1M aq Na$_2$CO$_3$ solution (5×50 mL), dried (MgSO$_4$) and concentrated in vacuo. The residue was purified by normal phase column chromatography (eluting with DCM, followed by a 100:8:1 mixture of DCM:EtOH:NH$_3$) to give 2-(4-methylpiperazin-1-yl)-ethyl 4-(4-chlorophenyl) piperazine-1-carboxylate (696 mg, 79%) as a colourless oil which crystallized on standing to give a white solid.

Analytical HPLC: purity 99.8% (System A, $R_T$=4.16 min); Analytical LCMS: purity 100% (System A, $R_T$=5.89 min), ES$^+$: 367.5 [MH]$^+$; HRMS calcd for $C_{19}H_{27}ClN_4O_2$: 366.1823, found 366.1836

Example 18

2-(4-Methylpiperazin-1-yl)ethyl 4-(3-trifluoromethylphenyl)piperazine-1-carboxylate

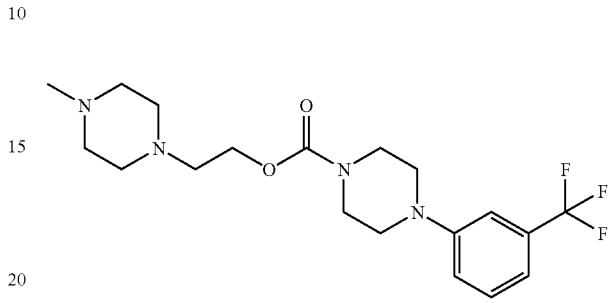

2-(4-Methylpiperazin-1-yl)ethyl 4-nitrophenyl carbonate (Intermediate 4; 761 mg, 2.5 mmol) was dissolved in DMF (20 mL). NEt$_3$ (0.4 mL, 2.9 mmol) and 4-(3-trifluoromethylphenyl)piperazine (583 mg, 2.5 mmol) were added and the reaction mixture was stirred at room temperature for 24 hours, the reaction mixture was then concentrated in vacuo. The resulting residue was dissolved in EtOAc (50 mL) and washed with 1 M aq Na$_2$CO$_3$ solution (5×50 mL), dried (MgSO$_4$) and concentrated in vacuo. The residue was purified by normal phase column chromatography (eluting with DCM, followed by a 100:8:1 mixture of DCM:EtOH:NH$_3$) to give 2-(4-methylpiperazin-1-yl)ethyl 4-(3-trifluoromethylphenyl)piperazine-1-carboxylate (631 mg, 64%) as a colourless oil.

Analytical HPLC: purity 100% (System A, $R_T$=4.55 min); Analytical LCMS: purity 100% (System A, $R_T$=6.19 min), ES$^+$: 401.5 [MH]$^+$; HRMS calcd for $C_{19}H_{27}F_3N_4O_2$: 400.2086, found 400.2100.

Example 19

2-(4-Methylpiperazin-1-yl)ethyl 4-(3-fluorophenyl) piperazine-1-carboxylate trihydrochloride

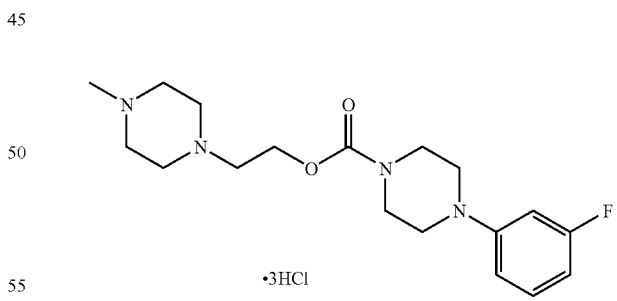

2-(4-Methylpiperazin-1-yl)ethyl 4-nitrophenyl carbonate (Intermediate 4; 2.3 g, 6.0 mmol) was dissolved in DMF (20 mL). DIPEA (0.76 mL, 4.4 mmol) and 4-(3-fluorophenyl)-piperazine (790 mg, 4.4 mmol) were added and the reaction mixture was stirred at room temperature for 24 hours, the reaction mixture was then concentrated in vacuo. The residue was purified by normal phase column chromatography (eluting with DCM, followed by a 95:5 mixture of DCM:MeOH) followed by reverse phase column chromatography (gradient eluting with MeOH in water, with 1% formic acid in each solvent, 0-50%). The resulting residue was dissolved in EtOAc (70 mL) and washed with 1M aq $Na_2CO_3$ solution (8×20 mL) and concentrated in vacuo. The residue was dissolved in DCM (10 mL) and 2M HCl in $Et_2O$ (3 mL) was added. The reaction mixture was then concentrated 1 in vacuo to give 2-(4-methylpiperazin-1-yl)ethyl 4-(3-fluorophenyl)piperazine-1-carboxylate trihydrochloride (106 mg, 6%) as an off-white solid.

Analytical HPLC: purity 99.4% (System A, $R_T$=4.08 min); Analytical LCMS: purity 100% (System A, $R_T$=5.65 min), $ES^+$: 351.5 $[MH]^+$; HRMS calcd for $C_{18}H_{27}FN_4O_2$: 350.2118, found 350.2128.

Example 20

2-(4-Methylpiperazin-1-yl)ethyl 4-(2-methylphenyl)piperazine-1-carboxylate

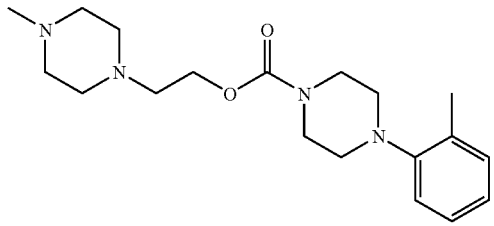

2-(4-Methylpiperazin-1-yl)ethyl 4-nitrophenyl carbonate (Intermediate 4; 866 mg, 2.8 mmol) was dissolved in DMF (20 mL). $NEt_3$ (1.5 mL, 10.8 mmol) and 4-(2-methyl-phenyl)piperazine dihydrochloride (704 mg, 2.8 mmol) were added and the reaction mixture was stirred at room temperature for 24 hours, and the reaction mixture was then concentrated in vacuo. The resulting residue was dissolved in EtOAc (50 mL) and washed with 1 M aq $Na_2CO_3$ solution (5×50 mL), dried ($MgSO_4$) and concentrated in vacuo. The residue was purified by normal phase column chromatography (eluting with DCM, followed by a 200:8:1 mixture of DCM:EtOH:$NH_3$) to give 2-(4-methylpiperazin-1-yl)-ethyl 4-(2-methylphenyl)piperazine-1-carboxylate (308 mg, 32%) as a yellow oil.

Analytical HPLC: purity 99.7% (System A, $R_T$=4.01 min); Analytical LCMS: purity 100% (System A, $R_T$=5.72 min), $ES^+$: 347.5 $[MH]^+$; HRMS calcd for $C_{19}H_{30}N_4O_2$: 346.2369, found 346.2380.

Example 21

2-(4-Methylpiperazin-1-yl)ethyl 4-(4-methylphenyl)piperazine-1-carboxylate

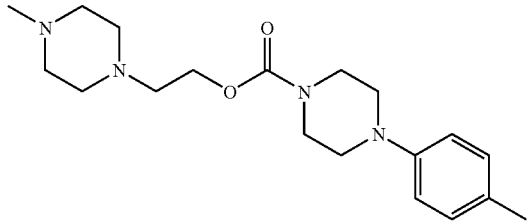

2-(4-Methylpiperazin-1-yl)ethyl 4-nitrophenyl carbonate (Intermediate 4; 866 mg, 2.8 mmol) was dissolved in DMF (25 mL). $NEt_3$ (1.5 mL, 10.8 mmol) and 4-(4-methyl-phenyl)piperazine dihydrochloride (724 mg, 2.9 mmol) were added and the reaction mixture was stirred at room temperature for 24 hours, and the reaction mixture was then concentrated in vacuo. The resulting residue was dissolved in EtOAc (50 mL) and washed with 1M aq $Na_2CO_3$ solution (5×50 mL), dried ($MgSO_4$) and concentrated in vacuo. The residue was purified by normal phase column chromatography (eluting with DCM, followed by a 200:8:1 mixture of DCM:EtOH:$NH_3$) to give 2-(4-methylpiperazin-1-yl)-ethyl 4-(4-methylphenyl)piperazine-1-carboxylate (293 mg, 30%) as a yellow oil.

Analytical HPLC: purity 99.8% (System A, $R_T$=3.46 min); Analytical LCMS: purity 100% (System A, $R_T$=5.15 min), $ES^+$: 347.6 [MH]; HRMS calcd for $C_{19}H_{30}N_4O_2$: 346.2369 found 346.2381.

Example 22

2-(4-Methylpiperazin-1-yl)ethyl 4-(2,5-dimethylphenyl)piperazine-1-carboxylate

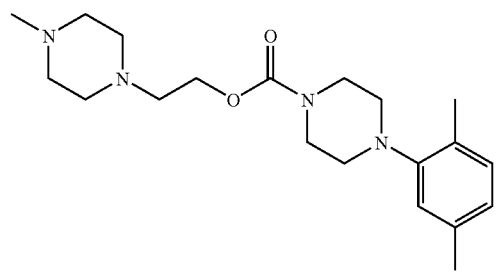

2-(4-Methylpiperazin-1-yl)ethyl 4-nitrophenyl carbonate (Intermediate 4; 866 mg, 2.8 mmol) was dissolved in DMF (25 mL). $NEt_3$ (0.5 mL, 3.6 mmol) and 4-(2,5-dimethylphenyl)piperazine (580 mg, 3.1 mmol) were added and the reaction mixture was stirred at room temperature for 24 hours, and the reaction mixture was then concentrated in vacuo. The resulting residue was dissolved in EtOAc (50 mL) and washed with 1M aq $Na_2CO_3$ solution (5×50 mL), dried ($MgSO_4$) and concentrated in vacuo. The residue was purified by normal phase column chromatography (eluting with DCM, followed by a 200:8:1 mixture of DCM:EtOH:$NH_3$) to give 2-(4-methylpiperazin-1-yl)ethyl 4-(2,5-dimethyl-phenyl)piperazine-1-carboxylate (274 mg, 27%) as a yellow oil.

Analytical HPLC: purity 99.4% (System A, $R_T$=4.19 min); Analytical LCMS: purity 99.5% (System A, $R_T$=5.89 min), $ES^+$: 361.6 [MH]; HRMS calcd for $C_{20}H_{32}N_4O_2$: 360.2525, found 360.2543.

Example 23

2-(4-methylpiperazin-1-yl)ethyl 4-(3,4-dichlorophenyl)piperazine-1-carboxylate trihydrochloride

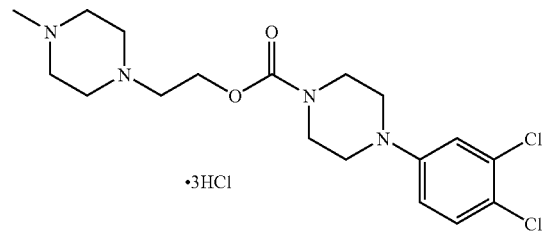

2-(4-Methylpiperazin-1-yl)ethyl 4-nitrophenyl carbonate (Intermediate 4; 680 mg, 2.2 mmol) was dissolved in DMF (20 mL). DIPEA (0.76 mL, 4.4 mmol) and 4-(3,4-dichlorophenyl)piperazine (508 mg, 2.2 mmol) were added and the reaction mixture was stirred at room temperature for 24 hours, and the reaction mixture was then concentrated in vacuo. The residue was purified by normal phase column chromatography (eluting with DCM, followed by a 400:8:1 mixture of DCM:EtOH:NH$_3$, followed by a 200:8:1 mixture of DCM:EtOH:NH$_3$) followed by reverse phase column chromatography (gradient eluting with MeOH in water, with 1% formic acid in each solvent, 0-100%). The residue was dissolved in DCM (10 mL) and 2M HCl in Et$_2$O (3 mL) was added. The reaction mixture was then concentrated in vacuo to give 2-(4-methylpiperazin-1-yl)ethyl 4-(3,4-dichlorophenyl)piperazine-1-carboxylate trihydrochloride (182 mg, 17%) as a white solid.

Analytical HPLC: purity 99.6% (System A, R$_T$=4.66 min); Analytical LCMS: purity 100% (System A, R$_T$=6.34 min), ES: 401.5 [MH]$^+$; HRMS calcd for Cis H$_{26}$Cl$_2$N$_4$O$_2$: 400.1433, found 400.1449.

Example 24

2-(4-Methylpiperazin-1-yl)ethyl 4-(2,4-difluorophenyl)piperazine-1-carboxylate trihydrochloride

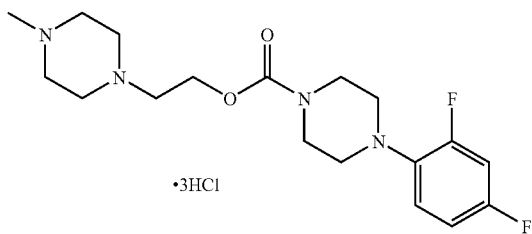

·3HCl 2-(4-Methylpiperazin-1-yl)ethyl 4-nitrophenyl carbonate (Intermediate 4; 680 mg, 2.2 mmol) was dissolved in DMF (20 mL). DIPEA (0.76 mL, 4.4 mmol) and 4-(2,4-difluorophenyl)piperazine (508 mg, 2.2 mmol) were added and the reaction mixture was stirred at room temperature for 24 hours, and the reaction mixture was then concentrated in vacuo. The residue was purified by normal phase column chromatography (eluting with DCM, followed by a 200:8:1 mixture of DCM:EtOH:NH$_3$) followed by reverse phase column chromatography (gradient eluting with MeOH in water, with 1% formic acid in each solvent, 0-100%). The residue was dissolved in DCM (10 mL) and 2M HCl in Et$_2$O (3 mL) was added. The reaction mixture was then concentrated in vacuo to give the title compound 2-(4-methylpiperazin-1-yl) ethyl 4-(2,4-difluorophenyl)piperazine-1-carboxylate trihydrochloride (630 mg, 65%) as a white solid.

Analytical HPLC: purity 100% (System A, R$_T$=4.02 min); Analytical LCMS: purity 100% (System A, R$_T$=5.76 min), ES$^+$: 369.5 [MH]$^+$; HRMS calcd for C$_{18}$H$_{26}$F$_2$N$_4$O$_2$: 368.2024, found 368.2038.

Example 25

2-(4-Methylpiperazin-1-yl)ethyl 4-(4-methoxyphenyl)piperazine-1-carboxylate

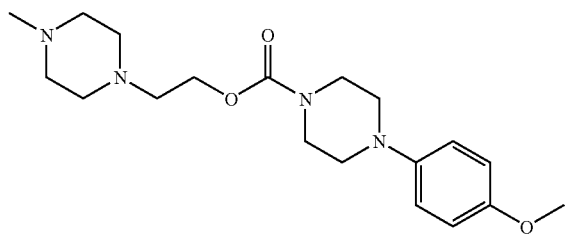

2-(4-Methylpiperazin-1-yl)ethyl 4-nitrophenyl carbonate (Intermediate 4; 680 mg, 2.2 mmol) was dissolved in DMF (20 mL). DIPEA (0.76 mL, 4.4 mmol) and 4-(4-methoxyphenyl)piperazine (422 mg, 2.2 mmol) were added and the reaction mixture was stirred at room temperature for 24 hours, and the reaction mixture was then concentrated in vacuo. The residue was purified by normal phase column chromatography (eluting with DCM, followed by a 500:8:1 mixture of DCM:EtOH:NH$_3$, followed by a 50:8:1 mixture of DCM:EtOH:NH$_3$). The residue was recrystallised from EtOAc to give 2-(4-methyl-piperazin-1-yl)ethyl 4-(4-methoxyphenyl)piperazine-1-carboxylate (137 mg, 17%) as a white solid.

Analytical HPLC: purity 99.2% (System A, R$_T$=3.20 min); Analytical LCMS: purity 99.1% (System A, R$_T$=4.87 min), ES$^+$: 363.6 [MH]$^+$; HRMS calcd for C$_{19}$H$_{30}$N$_4$O$_3$: 1362.2318, found 362.2330.

Example 26

2-(4-Methylpiperazin-1-yl)ethyl 3-methyl-4-(3-methylphenyl)piperazine-1-carboxylate

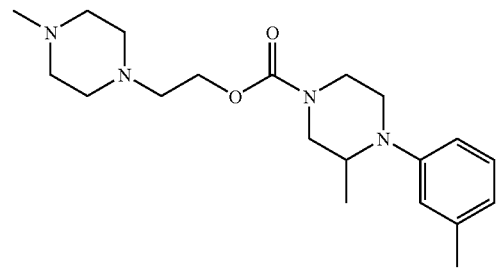

2-(4-Methylpiperazin-1-yl)ethyl 4-nitrophenyl carbonate (Intermediate 4; 2.56 g, 8.28 mmol) was dissolved in DMF (20 mL). DIPEA (1.40 mL, 8.45 mmol) and 2-Methyl-4-(3-methylphenyl)piperazine (1.50 g, 7.87 mmol) were added and the reaction mixture was stirred at room temperature for 24 hours, and the reaction mixture was then concentrated in vacuo. The resulting residue was dissolved in EtOAc (200 mL) and washed with 1 M aq Na$_2$CO$_3$ solution (6×100 mL), dried (MgSO$_4$) and concentrated in vacuo. The residue was purified by reverse phase chromatography (gradient eluting with MeOH in water, with 1% formic acid in each solvent, 0-30%). The resulting residue was dissolved in DCM (50 mL) and stirred with solid $K_2CO_3$ for 20 minutes, filtered and concentrated in vacuo, give 2-(4-methylpiperazin-1-yl)ethyl 3-methyl-4-(3-methylphenyl)piperazine-1-carboxylate (1.97 g, 69%) as a pale yellow oil.

Analytical HPLC: purity 100% (System A, $R_T$=3.29 min); Analytical LCMS: purity 100% (System A, $R_T$=4.91 min), ES$^+$: 361.6 [MH]$^+$; HRMS calcd for $C_{20}H_{32}N_4O_2$: 360.2525, found 360.2543.

Example 27

2-(4-Methylpiperazin-1-yl)ethyl 4-benzylpiperazine-1-carboxylate

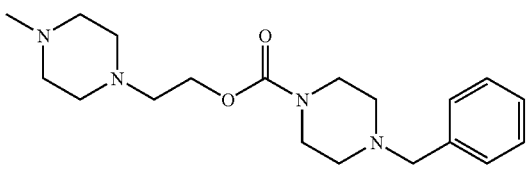

2-(4-Methylpiperazin-1-yl)ethyl 4-nitrophenyl carbonate (Intermediate 4; 567 mg, 1.8 mmol) was dissolved in DMF (15 mL). DIPEA (0.52 mL, 3.0 mmol) and 4-benzyl-piperazine (0.296 mL, 1.7 mmol) were added. The reaction mixture was stirred at room temperature for 24 hours and then concentrated in vacuo. The residue was dissolved in EtOAc (40 mL) and washed with 1 M aq $Na_2CO_3$ solution (6×50 mL), dried ($MgSO_4$) and concentrated in vacuo. The crude product was purified by reverse phase chromatography (gradient eluting with MeOH in water, 0-100%) to give 2-(4-methylpiperazin-1-yl)ethyl 4-benzylpiperazine-1-carboxylate (352 mg, 60% yield) as a colourless oil.

Analytical HPLC: purity 100% (System A, $R_T$=2.92/3.00 min, split peak); Analytical LCMS: purity 100% (System A, $R_T$=4.61 min), ES$^+$: 347.6 [MH]$^+$; HRMS calcd for $C_{19}H_{30}N_4O_2$: 346.2369, found 346.2383.

Example 28

2-(4-Methylpiperazin-1-yl)ethyl 4-phenylpiperidine-1-carboxylate formate

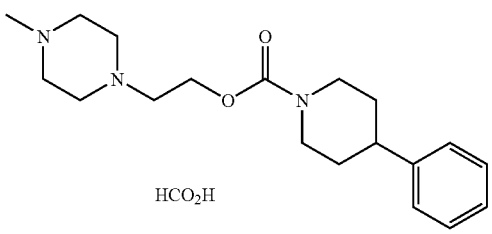

2-(4-Methylpiperazin-1-yl)ethyl 4-nitrophenyl carbonate (Intermediate 4; 680 mg, 2.2 mmol) was dissolved in DMF (20 mL). DIPEA (0.52 mL, 3.0 mmol) and 4-phenylpiperidine (322 mg, 2.0 mmol) were added and the reaction mixture was stirred at room temperature for 65 hours and then concentrated in vacuo. The residue was dissolved in EtOAc (40 mL) and washed with 1 M aq $Na_2CO_3$ solution (6×50 mL), dried ($MgSO_4$) and concentrated in vacuo. The crude product was purified by reverse phase column chromatography (gradient eluting with MeOH in water, with 1% formic acid in each solvent, 0-30%) to give 2-(4-methylpiperazin-1-yl)ethyl 4-phenylpiperidine-1-carboxylate formate (330 mg, 42%) as a yellow oil.

Analytical HPLC: purity 100% (System A, $R_T$=4.18 min); Analytical LCMS: purity 100% (System A, $R_T$=5.87 min), ES$^+$: 332.5 [MH]$^+$; HRMS calcd for $C_{19}H_{29}N_3O_2$: 331.2260, found 331.2271.

Example 29

2-(4-Methylpiperazin-1-yl)ethyl 3-phenylpyrrolidine-1-carboxylate

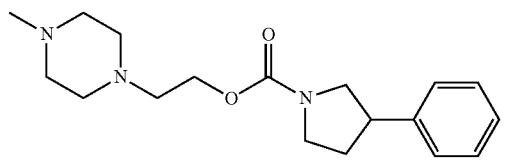

2-(4-Methylpiperazin-1-yl)ethyl 4-nitrophenyl carbonate (Intermediate 4; 2.10 g, 6.79 mmol) was dissolved in DMF (30 mL). DIPEA (2.37 mL, 13.59 mmol) and 3-phenylpyrrolidine (1.00 g, 6.79 mmol) were added and the reaction mixture was stirred at room temperature for 4 hours, and the reaction mixture was then concentrated in vacuo. The resulting residue was dissolved in EtOAc (300 mL) and washed with 1M aq $Na_2CO_3$ solution (6×200 mL), brine (50 mL), dried ($MgSO_4$) and concentrated in vacuo. The residue was dissolved in DCM (100 mL) and methyl isocyanate resin (2.0 g) was added, the reaction mixture shaken for 14 h, filtered and then concentrated in vacuo. The residue was purified by reverse phase chromatography (gradient eluting with MeOH in water, with 1% formic acid in each solvent, 0-30%). The resulting residue was dissolved in DCM (60 mL) and stirred with solid $K_2CO_3$ for 20 minutes, filtered and concentrated in vacuo, to give 2-(4-methylpiperazin-1-yl)ethyl 3-phenylpyrrolidine-1-carboxylate (1.03 g, 48.0%) as a pale yellow oil.

Analytical HPLC: purity 100% (System A, $R_T$=3.85 min); Analytical LCMS: purity 100% (System A, $R_T$=5.04 min), ES$^+$: 318.5 [MH]$^+$; HRMS calcd for $C_{18}H_{27}N_3O_2$: 317.2103, found 317.2114.

Example 30

2-piperazin-1-ylethyl 4-phenylpiperazine-1-carboxylate trihydrochloride

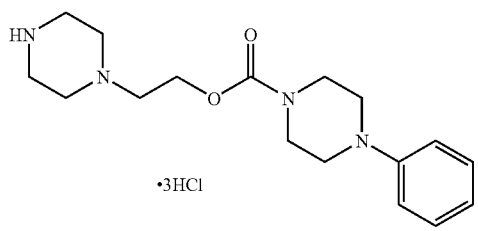

To a solution of 1-(2-hydroxyethyl)piperazine (51.7 g, 398 mmol) in DCM (500 mL) was added NEt$_3$ (70.0 mL, 526 mmol) and di-tert-butyl dicarbonate (80.0 g, 367 mmol). The reaction mixture was stirred overnight at room temperature then washed with 1 M aq $Na_2CO_3$ solution (2×300 mL), dried ($MgSO_4$) and concentrated in vacuo to give tert-butyl 4-(2-hydroxyethyl)piperazine-1-carboxylate (66.0 g, 72%) as a colourless oil.

Analytical LCMS: (System D $R_T$=1.54 min), $ES^+$: 231.4 [MH]-4.

Bis(p-nitrophenyl)carbonate (1.52 g, 5.0 mmol) was dissolved in DCM (20 mL). tert-Butyl 4-(2-hydroxyethyl)piperazine-1-carboxylate from the previous step (1.15 g, 5.0 mmol) and NMM (0.55 mL, 5.0 mmol) were added and the reaction mixture was stirred at room temperature for 16 hours. The reaction mixture was diluted with DCM (40 mL) and washed with sat aq $NaHCO_3$ solution (5×50 mL), dried ($Na_2SO_4$) and concentrated in vacuo to give a yellow oil. The oil was purified by recrystallisation from EtOAc and heptane to give 2-(4-(tert-butoxycarbonyl)piperazin-1-yl)ethyl 4-nitrophenyl carbonate (1.208 g, 61%) as an orange solid.

Analytical LCMS: (System C $R_T$=1.90 min), $ES^+$: 396.5 [MH]−.

2-(4-(tert-Butoxycarbonyl)piperazin-1-yl)ethyl 4-nitrophenyl carbonate (7.01 g, 17.7 mmol) was dissolved in DMF (150 mL). Phenylpiperazine (2.8 mL, 18.3 mmol) and $NEt_3$ (3.0 mL, 21.5 mmol) were added and the reaction mixture was stirred at room temperature for 18 hours. The reaction mixture was concentrated in vacuo, dissolved in EtOAc (250 mL), washed with 1M aq $Na_2CO_3$ solution (5×250 mL), dried ($MgSO_4$) and concentrated in vacuo. The residue was purified by reverse phase chromatography (gradient eluting with MeOH in water, 0-100%) to give 2-(4-(tert-butoxycarbonyl) piperazin-1-yl)ethyl 4-phenyl-piperazine-1-carboxylate (5.68 g, 77%) as a yellow oil. 2-(4-(tert-Butoxycarbonyl)-piperazin-1-yl)ethyl 4-phenylpiperazine-1-carboxylate (0.45 g, 1.07 mmol) was dissolved in a mixture of DCM (30 mL) and 2M HCl in $Et_2O$ (4 mL, 8 mmol) and stirred overnight. The supernatant was discarded. The residue washed with DCM (3×15 mL) and dried in vacuo to give 2-(piperazin-1-yl)ethyl 4-phenylpiperazine-1-carboxylate trihydrochloride (0.42 g, 98%) as a pale brown glass.

Analytical HPLC: purity 100% (System A, $R_T$=3.42 min); Analytical LCMS: purity 100% (System A, $R_T$=3.92 min), $ES^+$: 319.1 $[MH]^+$.

Example 31

2-(4-(2-Methoxyethyl)piperazin-1-yl)ethyl 4-phenylpiperazine-1-carboxylate

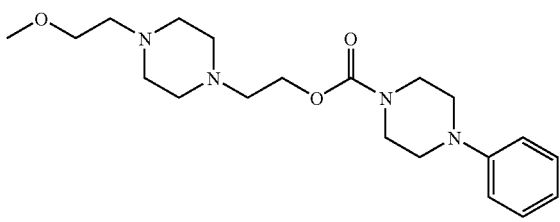

2-(piperazin-1-yl)ethyl 4-phenylpiperazine-1-carboxylate (None HCl salt of Example 30; 311 mg, 0.98 mmol) was dissolved in DMF (2 mL). 2-bromoethyl methyl ether (92 µl, 0.98 mmol) and DIPEA (0.3 mL, 1.72 mmol) were added and the reaction mixture was heated at 170° C. for 15 minutes in a Biotage Initiator microwave at high absorption. The reaction mixture was concentrated in vacuo, dissolved in 1 M aq $Na_2CO_3$ solution (25 mL) and extracted with DCM (3×25 mL), dried ($MgSO_4$) and concentrated in vacuo. The residue was purified by normal phase column chromatography (eluting with DCM, followed by a 200:8:1 mixture of DCM: $EtOH:NH_3$) to give 2-(4-(2-methoxyethyl)-piperazin-1-yl) ethyl 4-phenylpiperazine-1-carboxylate (163 mg, 44%) as a yellow oil.

Analytical HPLC: purity 98.6% (System A, $R_T$=3.48 min); Analytical LCMS: purity 98.1% (System A, $R_T$=5; 20 min), $ES^+$: 377.6 $[MH]^+$; HRMS calcd for $C_{20}H_{32}N_4O_3$: 376.2474, found 376.2493.

Example 32

2-(4-Ethylpiperazin-1-yl)ethyl 4-phenylpiperazine-1-carboxylate trihydrochloride

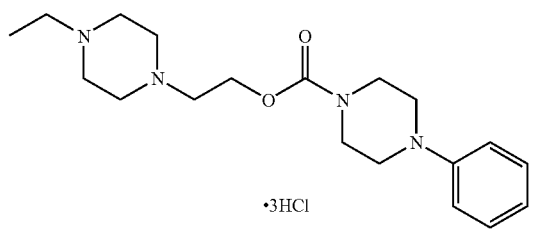

2-(piperazin-1-yl)ethyl 4-phenylpiperazine-1-carboxylate (None HCl salt of Example 30; 291 mg, 0.91 mmol) was dissolved in DMF (2 mL). Iodoethane (74 µl, 2.31 mmol) and DIPEA (0.3 mL, 1.72 mmol) were added and the reaction mixture was heated at 170° C. for 15 minutes in a Biotage Initiator microwave at high absorption and then concentrated in vacuo. The residue was dissolved in 1 M aq $Na_2CO_3$ solution (25 mL) and extracted with DCM (3×25 mL), dried ($MgSO_4$) and concentrated in vacuo. The crude product was purified normal phase column chromatography (eluting with DCM, followed by a 200:8:1 mixture of DCM:$EtOH:NH_3$) followed by reverse phase chromatography (gradient eluting with MeOH in water, with 1% formic acid in each solvent, 0-100%) to give a colourless oil. The oil was dissolved in DCM, treated with an excess of 2M HCl in $Et_2O$ and concentrated in vacuo to give 2-(4-ethylpiperazin-1-yl)ethyl 4-phenylpiperazine-1-carboxylate trihydrochloride (197 mg, 52%) as a white solid.

Analytical HPLC: purity 99.8% (System A, $R_T$=3.41 min); Analytical LCMS: purity 98.9% (System A, $R_T$=5.28 min), ES$^+$: 347.6 [MH]; HRMS calcd for $C_{19}H_{30}N_4O_2$: 346.2369, found 346.2379.

Example 33

2-(4-Methyl-1,4-diazepan-1-yl)ethyl 4-(4-methylphenyl)piperazine-1-carboxylate

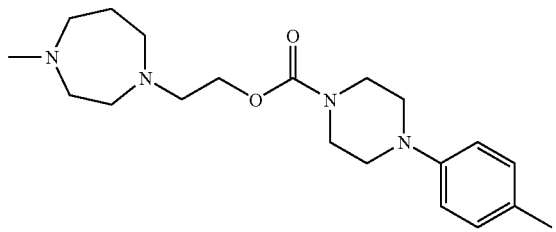

1-Methylhomopiperazine (2.00 g, 17.5 mmol) and DIPEA (3.0 mL, 18.4 mmol) were dissolved in DMF (25 mL). 2-bromethanol (1.3 mL, 18.4 mmol) was added slowly over 5 minutes. The reaction mixture was stirred at 100° C. for 2 hours and then at room temperature for 48 hours and then concentrated in vacuo. The residue was dissolved in EtOAc (~300 mL) and then washed sequentially with 1M aq $Na_2CO_3$ solution (5×200 mL), dried ($MgSO_4$) and concentrated in vacuo to give 2-(4-methylhomopiperazin-1-yl)ethanol (2.77 g, 100%) as a brown oil which was used without further purification.

Analytical LCMS: (System C, $R_T$=0.33 min), ES$^+$: 159.2 [MH]$^+$.

2-(4-methylhomopiperazin-1-yl)ethanol from the previous step (2.77 g, 17.5 mmol) was dissolved in DCM (25 mL) and cooled to 0° C. NMM (2.00 mL, 18.4 mmol) and p-nitrophenyl chloroformate (3.71 g, 18.4 mmol) were added. The reaction mixture was stirred at 0° C. for 30 minutes and then at room temperature for 2 hours. A solution of 4-(4-methylphenyl)piperazine dihydrochloride (2.84 g, 11.4 mmol) and DIPEA (5.50 mL, 33.3 mmol) in DMF (40 mL) was then added. The reaction mixture was stirred at room temperature for 3 h and then concentrated in vacuo. The residue was dissolved in EtOAc (300 mL) and then washed sequentially with 1 M aq $Na_2CO_3$ solution (5×200 mL), dried ($MgSO_4$) and concentrated in vacuo. The residue was purified by normal phase column chromatography (eluting with DCM, followed by a 85:15 mixture of DCM:MeOH) followed by reverse phase HPLC (Advanced Chromatography Technologies ACE-122-1030 RP silica 100×30 mm column, packed with Ace 5 C8 (5 μm), Pore Size 100 Å, 30 mL/min, gradient of actonitrile in water, with 0.1% trifluoroacetic acid in each solvent, 8-38%). The resulting residue was dissolved in DCM (50 mL) and stirred with solid $K_2CO_3$ for 20 minutes, filtered and concentrated in vacuo to give 2-(4-methyl-1,4-diazepan-1-yl)ethyl 4-(4-methylphenyl)piperazine-1-carboxylate (184 mg, 3.0%) as a pale yellow oil.

Analytical HPLC: purity 98.1% (System A, $R_T$=3.50 min), Analytical LCMS: purity 95.8% (System A, $R_T$=3.96 min), ES$^+$: 361.2 [MH]$^+$; HRMS calcd for $C_{20}H_{32}N_4O_2$: 360.2525, found 360.2542.

Example 34

3-(4-Methylpiperazin-1-yl)propyl 4-phenylpiperazine-1-carboxylate

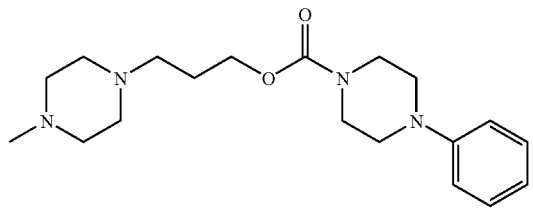

1-(3-Hydroxypropyl)-4-piperazine (0.63 g, 4.0 mmol) was dissolved in DCM (30 mL) and cooled to 0° C. DIPEA (1.39 mL, 8.0 mmol) and p-nitrophenyl chloroformate (0.80 g, 4.0 mmol) were added. The reaction mixture was stirred at room temperature for 2 hours and then phenylpiperazine (0.61 mL, 4.0 mmol) was added. The reaction mixture was stirred at room temperature for 16 hours and then concentrated in vacuo. The residue was dissolved in EtOAc (100 mL) and washed sequentially with 1M aq $Na_2CO_3$ solution (4×100 mL), and concentrated in vacuo. The residue was purified by reverse phase chromatography (gradient eluting with MeOH in water, with 1% formic acid in each solvent, 0-30%). The resulting residue was dissolved in DCM (30 mL) and stirred with solid $Na_2CO_3$ for 20 minutes, filtered and concentrated in vacuo. The resulting residue was purified by reverse phase HPLC (gradient eluting with acetonitrile in water, 5-45%) to give 3-(4-methyl-piperazin-1-yl)propyl 4-phenylpiperazine-1-carboxylate (148 mg, 11%) as a colourless oil.

Analytical HPLC: purity 100% (System A, $R_T$=3.51 min); Analytical LCMS: purity 100% (System A, R-T=3.99 min), ES$^+$: 347.2 [MH]$^+$; HRMS calcd for $C_{19}H_{30}N_4O_2$: 346.2369, found 346.2386.

Example 35

1-[2,2-Dimethyl-3-(4-methylpiperazin-1-yl)propanoyl]-4-phenylpiperazine

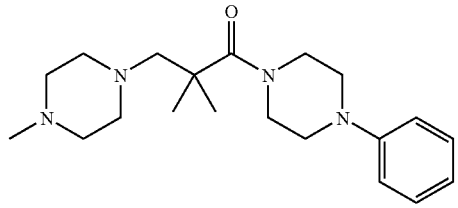

3-Bromo-2,2-dimethylpropionic acid (2.07 g, 11.4 mmol) was dissolved in DCM (12 mL). Oxalyl chloride (1.50 mL, 17.2 mmol) was added slowly over 10 minutes. The reaction mixture was stirred at room temperature for 3.5 hours and then concentrated in vacuo. The residue was dissolved in DCM (10 mL) and added to a solution of phenyl piperazine (1.74 mL, 11.4 mmol) and DIPEA (3.0 mL, 17.2 mmol) in DCM (20 mL) at 0° C. The reaction mixture, was allowed to warm to room temperature over 1 hour and then stirred at room temperature for 16 hours. The reaction mixture was washed with 10% citric acid solution (2×50 mL), dried (MgSO$_4$) and concentrated in vacuo. The resulting residue was purified using normal phase column chromatography (eluting with heptane, followed by a 1:1 mixture of EtOAc:heptane) to give 3-bromo-1-(4-phenyl)piperazine-2,2-dimethylpropan-1-one (1.36 g, 37%) as a yellow oil.

Analytical LCMS: purity ~80% (System C, R$_T$=2.14 min), ES$^+$: 326.2 [MH]$^+$.

3-Bromo-1-(4-phenyl)piperazine-2,2-dimethylpropan-1-one (1.36 g, 4.2 mmol) was dissolved in N-methylpyrrolidinone (3 mL). N-Methylpiperazine (0.93 mL, 8.36 mmol) was added and the reaction mixture was heated at 200° C. for 15 minutes in a Biotage Initiator microwave at normal absorption. The reaction mixture was purified by reverse phase column chromatography (gradient eluting with MeOH in water, with 1% formic acid in each solvent, 0-30%). The resulting residue was dissolved in DCM (100 mL) and stirred with solid K$_2$CO$_3$ for 20 minutes, filtered and concentrated in vacuo to give 1-[2,2-dimethyl-3-(4-methylpiperazin-1-yl)propanoyl]-4-phenylpiperazine (547 mg, 38%) as a yellow oil.

Analytical HPLC: purity 99.9% (System A, R$_T$=3.46 min); Analytical LCMS: purity 99.3% (System A, R$_T$=4.64 min), ES$^+$: 345.6 [MH]$^+$; HRMS calcd for C$_{20}$H$_{32}$N$_4$O: 344.2576, found 344.2588.

Example 36

1-{2,2-Dimethyl-3-[4-(4-chlorophenyl)piperazin-1-yl]-3-oxopropyl}-4-methylpiperazine

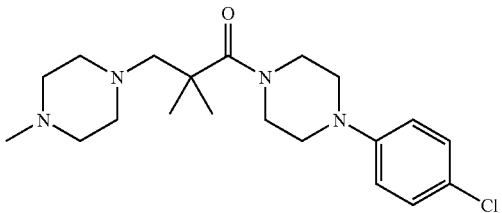

3-Bromo-2,2-dimethylpropionic acid (1.50 g, 8.29 mmol) was dissolved in thionyl chloride (10 mL) and DMF (0.1 mL). The reaction mixture was heated at reflux for 1.5 hours and then concentrated in vacuo, The residue was dissolved in DCM (10 mL) and added to a solution of 4-chlorophenyl piperazine dihydrochloride (2.35 g, 8.70 mmol) and DIPEA (5.05 mL, 29.0 mmol) in DCM (20 mL) at 0° C. The reaction mixture was stirred at 0° C. for 2 hours and then concentrated in vacuo. The residue was dissolved in DCM (100 mL) and washed with 10% citric acid solution (50 mL), sat aq NaHCO$_3$ solution (50 mL), brine (50 mL), dried (MgSO$_4$) and concentrated in vacuo. The resulting residue was purified using normal phase column chromatography (eluting with heptane, followed by a 1:1 mixture of EtOAc:heptane) to give 3-bromo-1-(4-chlorophenyl)piperazine-2,2-dimethyl-propan-1-one (0.87 g, 29.3%) as a yellow solid.

Analytical LCMS: purity ~75% (System C, R$_T$=2.40 min), ES$^+$: 361.3 [MH]$^+$.

3-Bromo-1-(4-chlorophenyl)piperazine-2,2-dimethylpropan-1-one (0.87 g, 2.43 mmol) was dissolved in N-methylpyrrolidinone (3 mL). N-Methylpiperazine (0.54 mL, 4.85 mmol) was added and the reaction mixture was heated at 200° C. for 15 minutes in a Biotage Initiator microwave at normal absorption. The reaction mixture was purified by reverse phase column chromatography (gradient eluting with MeOH in water, with 1% formic acid in each solvent, 0-30%). The resulting residue was dissolved in DCM (100 mL) and stirred with solid K$_2$CO$_3$ for 20 minutes, filtered and concentrated ill vacuo, to give a pale brown oil which was recrystallised from heptane to give 1-{2,2-dimethyl-3-[4-(4-chlorophenyl)piperazin-1-yl]-3-oxopropyl}-4-methylpiperazine (335 mg, 36.4%) as a white solid.

Analytical HPLC: purity 99.8% (System A, R$_T$=4.36 min); Analytical LCMS: purity 100% (System A, R$_T$=6.34 min), ES$^+$: 379.4 [MH]$^+$; HRMS calcd for C$_{20}$H$_{31}$ClN$_4$O: 378.2186, found 378.2196.

Example 37

1-{2,2-Dimethyl-3-[4-(4-methylphenyl)piperazin-1-yl]-3-oxopropyl}-4-methylpiperazine

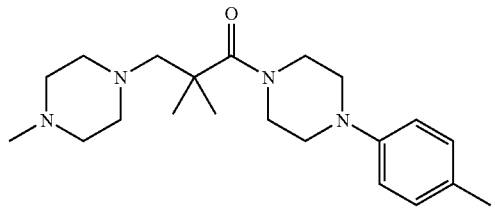

3-Bromo-2,2-dimethylpropionic acid (10.0 g, 55.3 mmol) was dissolved in DCM (60 mL). Oxalyl chloride (7.20 mL, 82.9 mmol) was added slowly over 10 minutes. The reaction mixture was stirred at room temperature for 18 hours and then concentrated in vacuo. The residue was dissolved in DCM (40 mL) and added to a solution of 4-methylphenyl-piperazine dihydrochloride (13.76 g, 55.3 mmol) and DIPEA (33.0 mL, 193.4 mmol) in DCM (100 mL) at 0° C. The reaction mixture was allowed to warm to room temperature over 1 hour and then stirred at room temperature for 16 hours. The reaction mixture was washed with 10% citric acid solution (2×100 mL), dried (MgSO$_4$) and concentrated in vacuo to give 3-bromo-1-(4-methylphenyl)piperazine-2,2-dimethylpropan-1-one (9.62 g, 52%) as a white solid which was used without further purification.

Analytical LCMS: purity ~70% (System C, R$_T$=2.34 min), ES$^+$: 339.3 [MH]$^+$.

3-Bromo-1-(4-methylphenyl)piperazine-2,2-dimethylpropan-1-one (6.00 g, 17.68 mmol) was dissolved in N-methylpyrrolidinone (12 mL). N-Methylpiperazine (4.12 mL, 37.94 mmol) was added. The reaction mixture was split into four batches and each was heated at 200° C. for 15 minutes in a Biotage Initiator microwave at high absorption. The reaction mixtures were combined and dissolved in DCM (300 mL), and washed with a 0.5M aq KOH solution (100 mL), water (100 mL), brine (100 mL), and then dried (MgSO$_4$) and concentrated in vacuo. The residue was dissolved in DCM (100 mL) and methyl isocyanate resin (2.0 g) was added, and the reaction mixture was shaken for 48 hours, filtered and then concentrated in vacuo. The resulting residue was purified by reverse phase chromatography (gradient eluting with MeOH in water, with 1% formic acid in each solvent, 0-30%). The resulting residue was dissolved in DCM (100 mL) and stirred with solid K$_2$CO$_3$ for 20 minutes, filtered and concentrated in vacuo, to give a pale brown oil which was recrystallised from heptane to give 1-{2,2-dimethyl-3-[4-(4-methylphenyl)-piperazin-1-yl]-3-oxopropyl}-4-methylpiperazine (1.47 g, 23.2%) as a white solid.

Analytical HPLC: purity 99.7% (System A, Rr=3.54 min); Analytical LCMS: purity 100% (System A, R$_T$=4.81 min), ES$^+$: 359.5 [MH]$^+$.

Example 38

1-{2,2-Dimethyl-3-[4-(4-methylphenyl)piperazin-1-yl]-3-oxopropyl}-4-ethylpiperazine

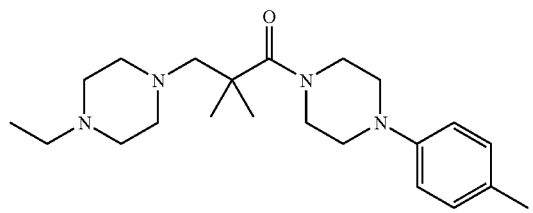

3-Bromo-1-(4-methylphenyl)piperazine-2,2-dimethyl-propan-1-one (Example 37, step 1; 2.00 g, 5.92 mmol) was dissolved in N-methylpyrrolidinone (10 mL). N-Ethylpiperazine (1.50 mL, 11.8 mmol) was added. The reaction mixture was split into four batches and each was heated at 200° C. for 15 minutes in a Biotage Initiator microwave at high absorption. The reaction mixtures were combined and dissolved in DCM (300 mL), and washed with water (2×80 mL), brine (100 mL), dried (MgSO$_4$) and then concentrated in vacuo. The residue was purified by reverse phase column chromatography (gradient eluting with MeOH in water, with 1% formic acid in each solvent, 0-30%). The resulting residue was dissolved in DCM (100 mL) and stirred with solid K$_2$CO$_3$ for 20 minutes, filtered and concentrated in vacuo, to give a colourless oil which was recrystallised from heptane to give 1-{2,2-dimethyl-3-[4-(4-methylphenyl)piperazin-1-yl]-3-oxopropyl}-4-ethylpiperazine (1.19 g, 48%) as a white solid.

Analytical HPLC: purity 100% (System A, R$_T$=3.59 min); Analytical LCMS: purity 100% (System A, R$_T$=5.52 min), ES$^+$: 373.6 [MH]$^+$; HRMS calcd for C$_{22}$H$_{36}$N$_4$O: 372.2889, found 372.2904.

Example 39

1-[2,2-Dimethyl-3-(4-methylpiperazin-1-yl)propanoyl]-4-(4-fluorophenyl)piperazine

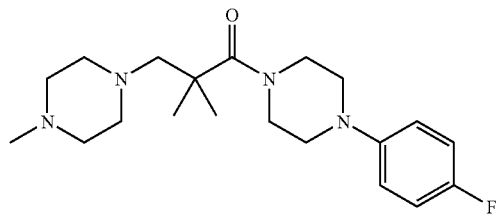

3-Bromo-2,2-dimethylpropionic acid (5.03 g, 27.8 mmol) was dissolved in DCM (60 mL). Oxalyl chloride (3.64 mL, 41.67 mmol) was added slowly over 10 minutes. The reaction mixture was stirred at room temperature for 18 hours and then concentrated in vacuo. The residue was dissolved in DCM (40 mL) and added to a solution of 4-fluorophenyl-piperazine (5.00 g, 27.8 mmol) and DIPEA (7.24 mL, 41.67 mmol) in DCM (30 mL) at 0° C. The reaction mixture was allowed to warm to room temperature over 1 hour and then stirred at room temperature for 16 hours. The reaction mixture was washed with 10% citric acid solution (2×100 mL), dried (MgSO$_4$) and concentrated in vacuo to give 3-bromo-1-(4-fluorophenyl)piperazine-2,2-dimethylpropan-1-one (8.04 g, 84%) as a yellow solid which was used without further purification.

Analytical LCMS: purity ~90% (System C, R$_T$=2.54 min), ES$^+$: 343.3 [MH]$^+$.

3-Bromo-1-(4-fluorophenyl)piperazine-2,2-dimethylpropan-1-one (2.00 g, 5.83 mmol) was dissolved in N-methylpyrrolidinone (10 mL). N-Methylpiperazine (1.30 mL, 11.7 mmol) was added. The reaction mixture was split into four batches and each was heated at 200° C. for 15 minutes in a Biotage Initiator microwave at high absorption. The reaction mixtures were combined and dissolved in DCM (100 mL), and washed with water (2×80 mL), dried (MgSO$_4$) and concentrated in vacuo. The resulting residue was purified by reverse phase column chromatography (gradient eluting with MeOH in water, with 1% formic acid in each solvent, 0-30%). The resulting residue was dissolved in DCM (100 mL) and stirred with solid Na$_2$CO$_3$ for 20 minutes, filtered and concentrated in vacuo, to give 1-[2,2-dimethyl-3-(4-methylpiperazin-1-yl)propanoyl]-4-(4-fluorophenyl)piperazine (451 mg, 21%) as a yellow oil.

Analytical HPLC: purity 100% (System A, R$_T$=3.68 min); Analytical LCMS: purity 98.2% (System A, R$_T$=5.52 min), ES$^+$: 363.5 [MH]$^+$; HRMS calcd for C$_{20}$H$_{31}$FN$_4$O: 362.2482, found 362.2499.

Example 40

1-Methyl-4-[(1-{[4-(4-methylphenyl)piperazin-1-yl]carbonyl}cyclopentyl)-methyl]piperazine

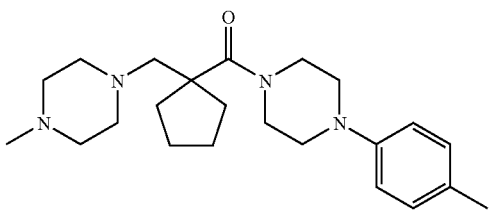

4-Methylphenyl piperazine dihydrochloride (4.20 g, 16.9 mmol) and NEt$_3$ (7.0 mL, 50.2 mmol) were dissolved in DCM (125 mL) at 0° C. Cyclopentanecarbonyl chloride (2.0 mL, 16.5 mmol) was added and the reaction mixture was allowed to warm to room temperature over 16 hours. The reaction mixture was washed with 1M aq Na$_2$CO$_3$ solution (3×100 mL), dried (MgSO$_4$) and concentrated in vacuo to give cyclopentanecarbonyl 4-(methyl)phenyl piperazine (4.42 g, 98%) as a pale brown oil which was used without further purification.

Analytical LCMS: purity 100% (System C, $R_T$=2.10 min), ES$^+$: 273.4 [MH]$^+$.

A 1.6 M n-butyl lithium solution in THF (15 mL, 24 mmol) was added drop-wise to a solution of diisopropylamine (4.0 mL, 28.6 mmol) in THF (100 mL) under argon at 0° C. The reaction mixture was stirred at 0° C. for 30 minutes and then cooled to −78° C. and a solution of cyclopentanecarbonyl 4-(methyl)phenyl piperazine (2.97 g, 10.9 mmol) in THF (10 mL) was added over 10 minutes. The reaction mixture was stirred at −78° C. for 5 hours and then a suspension of paraformaldehyde (0.90 g, 30 mmol) in THF (10 mL) was added. The reaction mixture was allowed to warm to room temperature over 1 hour and then stirred at room temperature for 16 hours. The reaction mixture was quenched with sat. aq NH$_4$Cl solution (10 mL), and then poured onto 1M aq Na$_2$CO$_3$ solution (500 mL) and extracted with EtOAc (2×500 mL). The organic layers were combined, dried (MgSO$_4$) and concentrated in vacuo to give a yellow oil which was recrystallised from heptane/EtOAc to give (1-hydroxymethyl-cyclopentyl)-(4-(4-methylphenyl)piperazin-1-yl)-methanone (2.11 g, 64%) as a pale yellow solid.

Analytical LCMS: purity 90% (System C, $R_T$=1.77 min), ES$^+$: 303.5 [MH]$^+$.

(1-Hydroxymethyl-cyclopentyl)-(4-(4-methylphenyl)piperazin-1-yl)-methanone from the previous step (1.57 g, 5.22 mmol) was dissolved in DCM (40 mL). Dess-Martin periodinane (3.06 g, 7.22 mmol) was added and the reaction mixture was stirred at room temperature for 3.5 hours. The reaction mixture diluted with Et$_2$O (100 mL) and 1M aq NaOH solution (50 mL) was added. The reaction mixture was stirred for 20 minutes and then the organic layer was separated and washed with 1M aq NaOH solution (50 mL), water (50 mL), dried (MgSO$_4$) and concentrated in vacuo to give 1-(4-(4-methylphenyl)-piperazine-1-carbonyl)-cyclopentanecarbaldehyde (1.64 g, 105%) as a brown oil which was used without further purification.

Analytical LCMS: purity ~80% (System C, $R_T$=2.02 min), ES$^+$: 301.5 [MH]$^+$.

1-(4-(4-Methylphenyl)-piperazine-1-carbonyl)-cyclopentanecarbaldehyde (1.64 g, 5.73 mmol) was dissolved in DCM (50 mL). Powdered molecular sieves (2.0 g) and acetic acid (0.1 mL) were added and the reaction mixture was stirred at room temperature for 1.5 hours and then sodium triacetoxyborohydride (2.44 g, 11.51 mmol) was added. The reaction mixture was stirred at room temperature for 16 hours and then quenched with 1M aq Na$_2$CO$_3$ solution (50 mL). The reaction mixture was stirred for 15 minutes and then the aqueous layer was separated and extracted with DCM (50 mL), the organic layers were combined, dried (MgSO$_4$) and concentrated in vacuo. The residue was purified by normal phase column chromatography (eluting with DCM, followed by a 95:4:1 mixture of DCM:EtOH:NH$_3$) followed by reverse phase column chromatography (gradient eluting with MeOH in water, with 1% formic acid in each solvent, 0-100%). The residue was dissolved in MeOH (5 mL) and added to 1M aq Na$_2$CO$_3$ solution (50 mL), and the aqueous layer was extracted with DCM (3×50 mL). The combined organic layers were dried (MgSO$_4$) and concentrated in vacuo to give 1-methyl-4-[(1-{[4-(4-methylphenyl)piperazin-1-yl]carbonyl}cyclopentyl)methyl]piperazine (520 mg, 26%) as a pale yellow solid.

Analytical HPLC: purity 99.7% (System A, $R_T$=4.25 min); Analytical LCMS: purity 99.3% (System A, $R_T$=4.77 min), ES$^+$: 385.6 [MH]$^+$; HRMS calcd for $C_{23}H_{36}N_4O$: 384.2889, found 384.2908.

Example 41

2-(4-Methylpiperazin-1-yl)ethyl 4-(4-fluorophenyl)piperazine-1-carboxylate

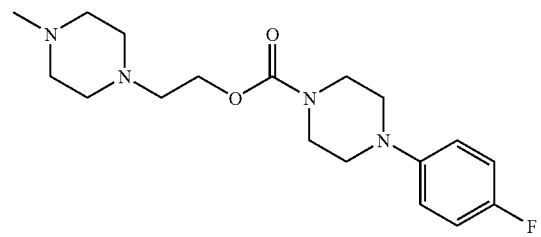

2-(4-Methyl-piperazin-1-yl)-ethanol (1.44 g, 10 mmol) was dissolved in anhydrous THF (50 mL) and the reaction mixture was cooled to 0° C. NaH (60% dispersion in oil; 0.40 g, 10 mmol) was added and stirred for 10 minutes and then 4-(4-fluorophenyl)-piperazine-1-carboxylic acid 4-nitrophenyl ester (3.45 g, 10 mmol) was added. The reaction mixture was stirred at room temperature overnight. The reaction mixture was cautiously quenched by the dropwise addition of a water (1 mL)/THF (10 mL) mixture. The THF was removed in vacuo and the residue was suspended between sat aq Na$_2$CO$_3$ solution (50 mL) and EtOAc (200 mL). The organic layer was washed with sat aq Na$_2$CO$_3$ solution (5×50 mL), dried (MgSO$_4$) and the solvent removed in vacuo.

The residue was initially purified by reverse phase column chromatography (LiChroprep RP-18, 40-63 μm, 460×26 mm (10 g), 30 mL/min, gradient 0% to 60% (over 60 min) MeOH in water). Further purification by reverse phase column chromatography in two batches (LiChroprep RP-18, 40-63 μm, 460×26 mm (100 g), 30 mL/min, gradient 0% to 20% (over 70 min) to 100% (over 5 min) MeOH in water with 1% formic acid) gave pure 2-(4-methylpiperazin-1-yl)ethyl 4-(4-fluorophenyl)piperazine-1-carboxylate formate. The formic acid was removed using K$_2$CO$_3$ in DCM and then dried in a vacuum oven overnight to give 2-(4-methylpiperazin-1-yl) ethyl 4-(4-fluorophenyl)piperazine-1-carboxylate (0.60 g, 17%) as a colourless gum.

Analytical HPLC: purity 99.5% (System A, $R_T$=3.70 min); Analytical LCMS: purity 100% (System A, $R_T$=4.08 min), ES$^+$: 351.1 [MH]$^+$; HRMS calcd for $C_{18}H_{27}FN_4O_2$: 350.2118, found 350.2133.

Example 42

2-(4-Methylpiperazin-1-yl)ethyl 4-(4-fluorobenzyl)piperazine-1-carboxylate

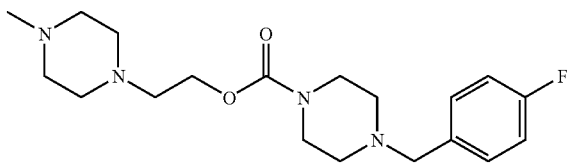

2-(4-Methyl-piperazin-1-yl)-ethanol (0.86 g, 6 mmol) and NMM (0.58 mL, 6 mmol) were dissolved in DCM (8 mL) and the reaction mixture was cooled to 0° C. 4-nitrophenyl chloroformate (1.29 g, 6 mmol) was added and the reaction mixture stirred for 1 h. To the reaction mixture was added a solution of 1-(4-fluoro-benzyl)-piperazine (0.97 g, 5 mmol) and DIPEA (6.0 mL, excess) in DMF (20 mL). The reaction mixture was stirred at room temperature overnight and then concentrated in vacuo. The residue was dissolved in EtOAc (150 mL), washed with sat aq Na$_2$CO$_3$ solution (6×100 mL), dried (MgSO$_4$) and the solvent removed in vacuo.

The residue was initially purified by column chromatography (normal phase, 20 g, Strata SI-1, silica gigatube, 20 mL/min, gradient 0% to 15% MeOH in DCM) and then further purified by reverse phase column chromatography (LiChroprep RP-18, 40-63 µm, 460×26 mm (100 g), 30 mL/min, gradient 0% to 30% (over 40 min) MeOH in water with 1% formic acid).

The residue was stirred for 2 h in DCM (10 mL) with K$_2$CO$_3$ (~0.20 g), filtered and then dried in a vacuum oven overnight to give 2-(4-methylpiperazin-1-yl)ethyl 4-(4-fluorobenzyl)piperazine-1-carboxylate (0.39 g, 21%) as a pale yellow oil.

Analytical HPLC: purity 99.7% (System A, $R_T$=3.09 min); Analytical LCMS: purity 100% (System A, $R_T$=3.55 min), ES$^+$: 365.6 [MH]$^+$; HRMS calcd for $C_{19}H_{29}FN_4O_2$: 364.2275, found 364.2292.

Example 43

2-(4-Methylpiperazin-1-yl)ethyl 4-(4-chlorobenzyl)piperazine-1-carboxylate

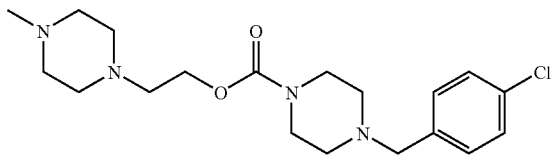

2-(4-Methyl-piperazin-1-yl)-ethanol (0.86 g, 6 mmol) and NMM (0.58 mL, 6 mmol) were dissolved in DCM (8 mL) and the reaction mixture was cooled to 0° C. 4-Nitrophenyl chloroformate (1.29 g, 6 mmol) was added and stirred for 1 h. To the reaction mixture was added a solution of 1-(4-chlorobenzyl)-piperazine (1.05 g, 5 mmol) and DIPEA (6.0 mL, excess) in DMF (20 mL). The reaction mixture was stirred at room temperature overnight and then concentrated in vacuo. The residue was dissolved in EtOAc (150 mL), washed with sat aq Na$_2$CO$_3$ solution (6×100 mL), dried (MgSO$_4$) and dried in vacuo.

The residue was initially purified by column chromatography (normal phase, 20 g, Strata SI-1, silica gigatube, 20 mL/min, gradient 0% to 15% MeOH in DCM) and then further purified by reverse phase column chromatography (LiChroprep RP-18, 40-63 µm, 460×26 mm (100 g), 30 mL/min, gradient 0% to 30% (over 40 min) MeOH in water with 1% formic acid).

The residue was stirred for 2 h in DCM (10 mL) with K$_2$CO$_3$ (~0.20 g), filtered and then dried in a vacuum oven overnight to give 2-(4-methylpiperazin-1-yl)ethyl 4-(4-chlorobenzyl)piperazine-1-carboxylate (0.51 g, 28%) as a pale yellow oil.

Analytical HPLC: purity 99.7% (System A, $R_T$=3.39 min); Analytical LCMS: purity 100% (System A, $R_T$=3.83 min), ES$^+$: 381.5 [MH]; HRMS calcd for $C_{19}H_{29}ClN_4O_2$: 380.1979, found 380.1996.

Example 44

2-(4-Methylpiperazin-1-yl)ethyl 4-[2-(4-chlorophenyl)ethyl]piperazine-1-carboxylate

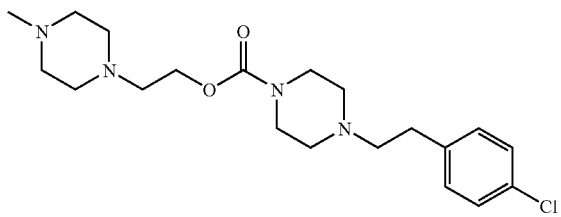

piperazine-1-carboxylic acid tert-butyl ester (1.0 g, 5.4 mmol) and DIPEA (1.9 mL, 10.8 mmol) were dissolved in DMF (20 mL) and then 1-(2-bromo-ethyl)-4-chloro-benzene (1.0 g, 4.6 mmol) was added. The reaction mixture was stirred at ambient temperature for 0.5 h and then concentrated in vacuo. The residue was dissolved in EtOAc (50 mL), washed with brine (2×50 mL), dried (MgSO$_4$) and the solvent removed in vacuo. The residue was dissolved in DCM (10 mL) and TFA (3 mL) overnight and then concentrated in vacuo. The crude 1-[2-(4-chloro-phenyl)-ethyl]-piperazine di-trifluoracetic acid was used in the next step without further purification.

2-(4-Methyl-piperazin-1-yl)-ethanol (663 mg, 4.6 mmol) and NMM (0.48 mL, 4.6 mmol) were dissolved in DCM (7 mL) and the reaction mixture was cooled to 0° C. 4-Nitrophenyl chloroformate (927 mg, 4.6 mmol) was added and the reaction mixture stirred for 1 h. To the reaction mixture was added a solution of 1-[2-(4-chloro-phenyl)-ethyl]-piperazine di-trifluoracetic acid (Step1; 4.6 mmol) and DIPEA (6.0 mL, excess) in DMF (20 mL). The reaction mixture was stirred at room temperature overnight and then concentrated in vacuo. The residue was dissolved in EtOAc (150 mL), washed with sat aq Na$_2$CO$_3$ solution (6×100 mL), dried (MgSO$_4$) and the solvent removed in vacuo.

The residue was initially purified by column chromatography (normal phase, 20 g, Strata is SI-1, silica gigatube, 20 mL/min, gradient 0% to 20% MeOH in DCM) and then further purified by reverse phase column chromatography (LiChroprep RP-18, 40-63 μm, 460×26 mm (100 g), 30 mL/min, gradient 0% to 30% (over 40 min) MeOH in water with 1% formic acid).

The residue was stirred for 2 h in DCM (10 mL) with $K_2CO_3$ (~0.20 g), filtered and then dried in a vacuum oven overnight to give 2-(4-methylpiperazin-1-yl)ethyl 4-[2-(4-chlorophenyl)ethyl]piperazine-1-carboxylate (116 mg, 6.4%) as a pale yellow oil.

Analytical HPLC: purity 97.1% (System A, $R_T$=3.64 min); Analytical LCMS: purity 100% (System A, $R_T$=5.15 min), $ES^+$: 395.5 $[MH]^+$; HRMS calcd for $C_{20}H_{31}ClN_4O_2$: 394.2136, found 394.2147.

Biological Tests

Animal Model of Human Obesity (Dietary-Induced Obese Rat)

Rodent models of obesity are valuable tools for studying the underlying factors that contribute to the initiation and maintenance of the obese state in humans. The model of diet-induced obesity (DIO) in rodents is particularly suited to this task as DIO rats share a number of traits with human obesity.

These include polygenic inheritance, insulin resistance, hyperleptinemia, lowered growth hormone secretion, proclivity to preferentially oxidize carbohydrate over fat, and the ability to decrease metabolic rate when calorie-restricted, leading to weight regain after restriction. In outbred rats fed a high energy diet, about one-half develop DIO, while the rest are resistant to obesity and gain no more weight than chow-fed controls (diet resistant, DR). The model of diet-induced obesity (DIO) is of special interest with regard to regulation of energy homeostasis. When fed a diet moderately high in fat, sucrose, and energy content (HE diet), about one-half of the rats will put on substantially more weight than the others (DIO vs. DR).

Rats predisposed to develop DIO will gain weight at rates comparable to rats fed a low-energy (chow) diet and will not become obese unless fed an HE diet. However, once the DIO and DR phenotypes are established on a HE diet, the resulting weight gains and body composition changes persist, even when animals are switched back to a normal chow diet. Changes in body weight and composition, which occur during the development and perpetuation of the DIO and DR phenotypes, are associated with several alterations in brain function that may underlie these adjustments.

DIO Protocol

The diet-induced obesity protocol as described by Widdowson, P. S. et al. (Diabetes (1997) 46:1782-1785) was followed for selection of obese-prone animals.

Wistar male rats (~200-250 g at start of modified dietary intervention) are put on a high-carbohydrate (HE) diet for 8-10 weeks. The composition of the diet is 33% (w/v) powdered chow (RM1), 33% (w/v) condensed milk (Nestle), 7% (w/v) Castor sugar (Tate & Lyle), and 27% (w/v) water. Body weights are recorded and following an 8-week period, animals are separated in 2 groups according to their weight. As in any outbred strain of animals (rodents, primates) a population will naturally separate in two groups: individuals prone to obesity (putting on more weight) or obesity-resistant (putting on less weight). The obese animals weigh up to 60 g more after 6 weeks. Obese-prone animals are kept to perform studies on the effect on body weight and food intake of compounds of formula (I). FIG. 1 shows an example of body weight separation between animals fed on the highly palatable diet (high carbohydrate).

In Vivo Experiments on the Effect of the Compounds on Body Weight

Obese-prone animals are treated with a compound of formula (I) and the effect on their body weight is measured. The compounds are dosed bid at 10 mg/kg PO, with a dose-volume of 1 mL/kg or an equivalent vehicle dose (saline) for comparison. The doses are administered AM (09:00) and PM (16:00) and the body weight is measured in the morning before dosing. There are typically 8 animals per group. FIGS. 2 to 5 show the cumulative body weight change (%) observed in a 4 day study in DIO rats for Examples 6, 16, 18 and 36, respectively.

Leptin Assay in Non-Recombinant System

Although well-characterised in recombinant systems (e.g. ObRb-transfected HEK293 cells), where leptin elicits a very marked increase in STAT3 phosphorylation, these systems have often failed to provide an accurate measure of activity of a test compound towards the leptin receptor. It seems that overexpression of the receptor (as well as the possibility for different drugs to act on different parts of the signaling pathway triggered by leptin association with its receptor) results in most cases in the absence of activity of the drugs tested.

The leptin receptor expression in non-recombinant system is often fluctuating and care must be given to identify a system where signal stability remains within experiments. Using such a system, leptin receptor antagonist mimetics could be identified by evaluating their action vs. leptin (see below).

Leptin is produced chiefly in adipose cells, but in humans, mRNA encoding leptin is also present in the placenta. Here, leptin might play an important proliferative role in the microvasculature. The possibility to use this hypothesis in a native cell line was evaluated.

JEG-3 Protocol

Figure 6:
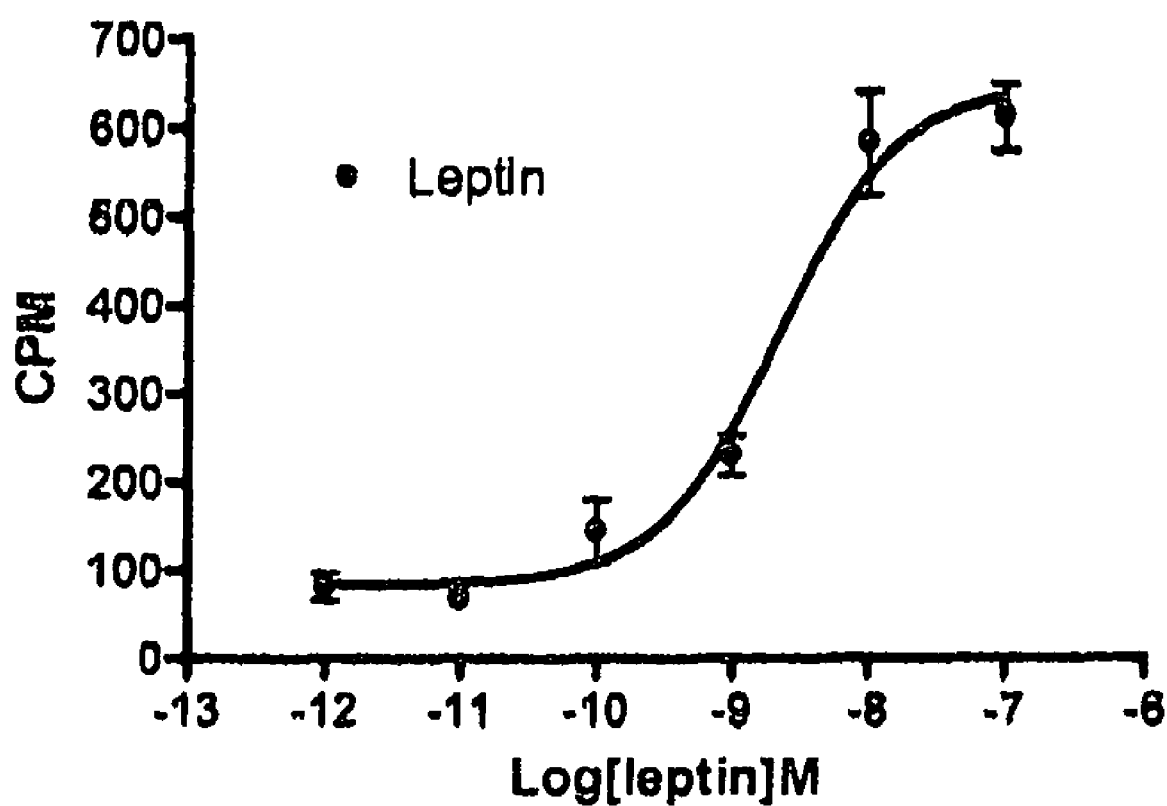
FIG. 6 shows the concentration-dependent increase in [$^3$H]-thymidine incorporation by JEG-3 cells for leptin.

In JEG-3 cells (choriocarcinoma cell line) leptin is able to stimulate proliferation up to 3 fold (Biol. Reprod. (2007) 76: 203-10). Leptin also causes a concentration-dependent increase in $[^3H]$-thymidine incorporation in JEG-3 cells (FIG. 6, maximal effect at 100 nM ($EC_{50}$=2.1 nM)). The radioactivity incorporated by the cells is an index of their proliferative activity and is measured in counts per minute (CPM) with a liquid scintillation beta counter.

This finding can be applied to test whether a compound is able to either reproduce the effect of leptin on cell proliferation (leptin receptor agonist mimetic) (i.e., a given compound will cause an increase in incorporated $[^3H]$-Thymidine by the cells) or to inhibit the effect of leptin (antagonistic effect) by preventing the leptin-mediated increase in $[^3H]$-thymidine incorporation.

This approach has the advantage of using a non-recombinant system and has reasonable reproducibility and robustness.

Measurement of Bra in Penetration

The test species (rodent) is given a bolus dose of the substrate under investigation, usually via intravenous (IV) or oral (PO) routes. At appropriate time points, blood samples are taken and the resultant plasma extracted and analysed for substrate concentration and, where appropriate, metabolite concentration. At similar time points, animals from another group are sacrificed, brains isolated and the brain surface cleaned. Brain samples are then homogenised, extracted and analysed for substrate concentration and, where appropriate, metabolite concentration. Alternatively, microdialysis probes are implanted into one or more brain regions of the test species and samples collected at appropriate time points for subsequent analysis. This method has the advantage of measuring only extra-cellular substrate concentration. Plasma and brain concentrations are then compared and ratios calculated, either by comparison of averaged concentrations at individual time points, or by calculation of the area-under-the-curve (AUC) of the concentration-time plots.

The invention claimed is:

1. A compound of formula (I)

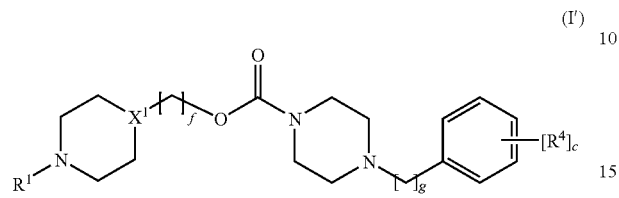

or a pharmaceutically acceptable salt thereof, wherein:

$X^1$ is selected from N and CH;

$R^1$ is selected from hydrogen, $C_{1-6}$-alkyl which is unsubstituted or optionally substituted with one or more substituents independently selected from halogen, hydroxy, cyano and $C_{1-6}$-alkoxy, and $C_{1-6}$-acyl which is unsubstituted or optionally substituted with one or more substituents independently selected from halogen, hydroxy and $C_{1-6}$-alkoxy attached to an atom other than the carbonyl carbon atom of the $C_{1-6}$-acyl;

each $R^4$ is independently selected from halogen, hydroxy, cyano, nitro, $CF_3$, $C_{1-6}$-alkyl and $C_{1-6}$-alkoxy;

c is 0, 1, 2 or 3;

f is 0, 1, 2 or 3; and g is 0, 1 or 2;

with the proviso that the compound or pharmaceutically acceptable salt thereof is not 2-(4-piperidinyl)ethyl 4-phenylpiperazine-1-carboxylate or a pharmaceutically acceptable salt thereof.

2. A compound according to claim 1, or a pharmaceutically acceptable salt thereof, wherein $R^1$ is selected from hydrogen, $C_{1-2}$-alkyl and $C_{1-2}$-alkoxy-$C_{1-2}$-alkyl.

3. A compound according to claim 1, or a pharmaceutically acceptable salt thereof, wherein c is 0, 1 or 2.

4. A compound according to claim 1, or a pharmaceutically acceptable salt thereof, wherein c is 1, 2 or 3 and each $R^4$ is independently selected from halogen, $CF_3$, $C_{1-2}$-alkyl and $C_{1-2}$-alkoxy.

5. A compound according to claim 1, or a pharmaceutically acceptable salt thereof, which is selected from (1-methylpiperidin-4-yl)methyl 4-phenylpiperazine-1-carboxylate;

(1-methylpiperidin-4-yl)methyl 4-(4-chlorophenyl)piperazine-1-carboxylate;

piperidin-4-ylmethyl 4-(4-methylphenyl)piperazine-1-carboxylate;

(1-methylpiperidin-4-yl)methyl 4-(4-methylphenyl)piperazine-1-carboxylate;

(1-methylpiperidin-4-yl)methyl 4-(3-methylphenyl)piperazine-1-carboxylate;

(1-methylpiperidin-4-yl)methyl 4-(4-fluorophenyl)piperazine-1-carboxylate;

(1-methylpiperidin-4-yl)methyl 4-(4-methoxyphenyl)piperazine-1-carboxylate;

[1-(2-methoxyethyl)piperidin-4-yl]methyl 4-phenylpiperazine-1-carboxylate;

[1-(2-methoxyethyl)piperidin-4-yl]methyl 4-(4-fluorophenyl)piperazine-1-carboxylate;

[1-(2-methoxyethyl)piperidin-4-yl]methyl 4-(4-chlorophenyl)piperazine-1-carboxylate;

[1-(2-methoxyethyl)piperidin-4-yl]methyl 4-(4-methylphenyl)piperazine-1-carboxylate;

[1-(2-methoxyethyl)piperidin-4-yl]methyl 4-(4-methoxyphenyl)piperazine-1-carboxylate;

2-(1-methylpiperidin-4-yl)ethyl 4-(4-methylphenyl)piperazine-1-carboxylate;

1-methylpiperidin-4-yl 4-(4-methylphenyl)piperazine-1-carboxylate;

2-(4-methylpiperazin-1-yl)ethyl 4-phenylpiperazine-1-carboxylate;

2-(4-methylpiperazin-1-yl)ethyl 4-(4-chlorophenyl)piperazine-1-carboxylate;

2-(4-methylpiperazin-1-yl)ethyl 4-(3-trifluoromethylphenyl)piperazine-1-carboxylate;

2-(4-methylpiperazin-1-yl)ethyl 4-(3-fluorophenyl)piperazine-1-carboxylate;

2-(4-methylpiperazin-1-yl)ethyl 4-(2-methylphenyl)piperazine-1-carboxylate;

2-(4-methylpiperazin-1-yl)ethyl 4-(4-methylphenyl)piperazine-1-carboxylate;

2-(4-methylpiperazin-1-yl)ethyl 4-(2,5-dimethylphenyl)piperazine-1-carboxylate;

2-(4-methylpiperazin-1-yl)ethyl 4-(3,4-dichlorophenyl)piperazine-1-carboxylate;

2-(4-methylpiperazin-1-yl)ethyl 4-(2,4-difluorophenyl)piperazine-1-carboxylate;

2-(4-methylpiperazin-1-yl)ethyl 4-(4-methoxyphenyl)piperazine-1-carboxylate;

2-(4-methylpiperazin-1-yl)ethyl 4-benzylpiperazine-1-carboxylate;

2-piperazin-1-ylethyl 4-phenylpiperazine-1-carboxylate;

2-(4-(2-methoxyethyl)piperazin-1-yl)ethyl 4-phenylpiperazine-1-carboxylate;

2-(4-ethylpiperazin-1-yl)ethyl 4-phenylpiperazine-1-carboxylate;

3-(4-methylpiperazin-1-yl)propyl 4-phenylpiperazine-1-carboxylate;

2-(4-methylpiperazin-1-yl)ethyl 4-(4-fluorophenyl)piperazine-1-carboxylate;

2-(4-methylpiperazin-1-yl)ethyl 4-(4-fluorobenzyl)piperazine-1-carboxylate;

2-(4-methylpiperazin-1-yl)ethyl 4-(4-chlorobenzyl)piperazine-1-carboxylate; and 2-(4-methylpiperazin-1-yl)ethyl 4-[2-(4-chlorophenyl)ethyl]piperazine-1-carboxylate;

and pharmaceutically acceptable salts thereof.

6. A pharmaceutical formulation containing a compound according to claim 1, or a pharmaceutically acceptable salt thereof, as an active ingredient, in combination with a pharmaceutically acceptable diluent or carrier.

7. A compound according to claim 1, or a pharmaceutically acceptable salt thereof, wherein $R^1$ is selected from hydrogen, $C_{1-4}$-alkyl and $C_{1-4}$-alkoxy-$C_{1-4}$-alkyl.

8. A compound according to claim 1, or a pharmaceutically acceptable salt thereof, wherein $R^1$ is selected from hydrogen, methyl, ethyl and methoxyethyl.

9. A compound according to claim 1, or a pharmaceutically acceptable salt thereof, wherein c is 1, 2 or 3 and each $R^4$ is independently selected from halogen, $CF_3$, $C_{1-4}$-alkyl and $C_{1-4}$-alkoxy.

10. A compound according to claim 1, or a pharmaceutically acceptable salt thereof, wherein c is 1, 2 or 3 and each $R^4$ is independently selected from fluoro, chloro, $CF_3$, methyl and methoxy.

11. A compound according to claim 1, or a pharmaceutically acceptable salt thereof, wherein f is 1 or 2.

12. A compound according to claim 1, or a pharmaceutically acceptable salt thereof, wherein g is 0.

13. A compound according to claim 1, or a pharmaceutically acceptable salt thereof, wherein c is 1, 2 or 3.

14. A method of treatment to reduce body weight, which comprises administering to a mammal, including man, in need of such treatment an effective amount of a compound according to claim 1, or a pharmaceutically acceptable salt thereof.

15. A method of treatment to reduce food intake, which comprises administering to a mammal, including man, in need of such treatment an effective amount of a compound according to claim 1, or a pharmaceutically acceptable salt thereof.

16. A method of treating obesity, which comprises administering to a mammal, including man, in need of such treatment an effective amount of a compound according to claim 1, or a pharmaceutically acceptable salt thereof.

17. A method of treating type 2 diabetes, which comprises administering to a mammal, including man, in need of such treatment an effective amount of a compound according to claim 1, or a pharmaceutically acceptable salt thereof.

* * * * *